(12) United States Patent
Tsuji et al.

(10) Patent No.: US 8,361,709 B2
(45) Date of Patent: Jan. 29, 2013

(54) METHOD OF PRODUCING TOOTH, SET OF TEETH, AND METHOD OF PRODUCING TISSUE

(75) Inventors: Takashi Tsuji, Nagareyama (JP); Kazuhisa Nakao, Tokyo (JP)

(73) Assignee: Organ Technologies Inc., Tokyo (JP)

( * ) Notice: Subject to any disclaimer, the term of this patent is extended or adjusted under 35 U.S.C. 154(b) by 1139 days.

(21) Appl. No.: 11/921,233

(22) PCT Filed: May 30, 2006

(86) PCT No.: PCT/JP2006/310805
§ 371 (c)(1),
(2), (4) Date: Feb. 13, 2008

(87) PCT Pub. No.: WO2006/129672
PCT Pub. Date: Dec. 7, 2006

(65) Prior Publication Data
US 2010/0021866 A1 Jan. 28, 2010

(30) Foreign Application Priority Data

May 30, 2005 (JP) ................................. 2005-157885
Mar. 1, 2006 (JP) ................................. 2006-055569

(51) Int. Cl.
*C12Q 1/68* (2006.01)
*A01N 1/00* (2006.01)
*C12N 5/00* (2006.01)
(52) U.S. Cl. .............................. 435/6; 435/1.1; 435/325
(58) Field of Classification Search .................... 435/1.1, 435/6, 325
See application file for complete search history.

(56) References Cited

U.S. PATENT DOCUMENTS

| | | | |
|---|---|---|---|
| 5,712,161 A | 1/1998 | Koezuka et al. | |
| 2002/0119180 A1 | 8/2002 | Yelick et al. | |
| 2004/0219489 A1 | 11/2004 | Yelick et al. | |
| 2006/0024249 A1* | 2/2006 | Yelick et al. | 424/50 |
| 2006/0121606 A1 | 6/2006 | Ito et al. | |
| 2007/0160584 A1* | 7/2007 | Ueda et al. | 424/93.7 |
| 2007/0231275 A1 | 10/2007 | Ueda | |

FOREIGN PATENT DOCUMENTS

| | | |
|---|---|---|
| CN | 1615162 A | 5/2005 |
| JP | A 6-141851 | 5/1994 |
| JP | A 2004-331557 | 11/2004 |
| JP | A 2004-357567 | 12/2004 |
| RU | 2217096 C1 | 11/2003 |
| WO | WO 95/18216 A1 | 7/1995 |
| WO | WO 01/60981 A1 | 8/2001 |
| WO | WO 2004/101774 A1 | 11/2004 |
| WO | WO 2005/014070 A1 | 2/2005 |
| WO | WO 2005/051436 A2 | 6/2005 |
| WO | WO 2006/000071 A1 | 1/2006 |
| WO | WO 2006/020240 A2 | 2/2006 |

OTHER PUBLICATIONS

Kenney et al. Patterns of Root and Alveolar-Bone Growth Associated with Development and Eruption of Teeth in Rhesus Monkeys. Journal of Dental Research, Mar.-Apr. 1969.*
International Search Report issued in International Patent Application No. 200718155-5, dated Feb. 18, 2010.
Written Opinion issued in International Patent Application No. 200718155-5, dated Mar. 19, 2010.
Mar. 26, 2010 Office Action issued in Russian Patent Application No. 2007148138/14(052749) (with English translation).
Chinese Office Action issued in Chinese Patent Application No. 200680019412.3 on Apr. 23, 2010 (with English translation).
Yamamoto, H. et al. "Analysis of Tooth Formation by Reaggregated Dental Mesenchyme from Mouse Embryo." *Journal Electron Microscopy*, vol. 52, No. 6, pp. 559-566 (2003).
Kagami, H. et al. "Potential of Regenerative Medicine by use of Tooth and Tooth Germ Derived Cells," *Regenerative Medicine*, vol. 4, No. 1, pp. 79-83 (2005).
Harada, H. et al. "Strategy on Regeneration of Teeth and Periodontal Tissues: Artificial Construction of Epithelial-Mesenchymal Interaction." *DE*, vol. 150, pp. 23-26 (2004).
Young, C.S. et al. "Tissue Engineering of Complex Tooth Structures of Biodegradable Polymer Scaffolds." *Journal of Dental Research*, vol. 81, No. 10, pp. 695-700 (202).
Honda, M. et al. "Preliminary Study of Tissue Engineered Odontogenesis in the Canine Jaw." *Regenerative Medicine*, vol. 4, No. 1, pp. 85-89 (2005).
Havlickova, B. et al. "Towards Optimization of an Organotypic Assay System that Imitates Human Hair Folliclelike Epithelial-Mesenchymal Interactions" *British Journal of Dermatology*, vol. 151, pp. 753-765 (2004).
Inamatsu, M. et al. "Establishment of Rat Dermal Papilla Cell Lines that Sustain the Potency to Induce Hair Follicles from Afollicular Skin" *Journal of Investigative Dermatology*, vol. 111, No. 5, pp. 767-776 (1998).
Matsumoto, K. et al. "Emerging Multipotent Aspects of Hepatocyte Growth Factor" *Journal of Biochemistry*, vol. 119, No. 4, pp. 591-600 (1996).
Ohazama, A. et al. "Stem-cell-based Tissue Engineering of Murine Teeth" *Journal of Dental Research*, vol. 83, No. 7, pp. 518-522 (2004).
Suzuki, H. et al. "Immunohistochemical Localization of Periostin in Tooth and Its Surrounding Tissues in Mouse Mandibles During Development" *The Anatomical Record Part A*, vol. 281A, pp. 1264-1275 (2004).

* cited by examiner

Primary Examiner — Karen Cochrane Carlson
Assistant Examiner — Natalie Moss
(74) Attorney, Agent, or Firm — Oliff & Berridge, PLC

(57) ABSTRACT

A first cell mass substantially containing only either one of mesenchymal cells or epithelial cells and a second cell mass substantially containing only the other one of the cells are positioned in contact with each other inside a support carrier which can maintain a condition of cell contact; and cultured to obtain a tooth having a specific cell placement. Preferably, after the culturing, the support carrier having both cell masses is cultured with kidney cells.

23 Claims, 20 Drawing Sheets

FIG.3
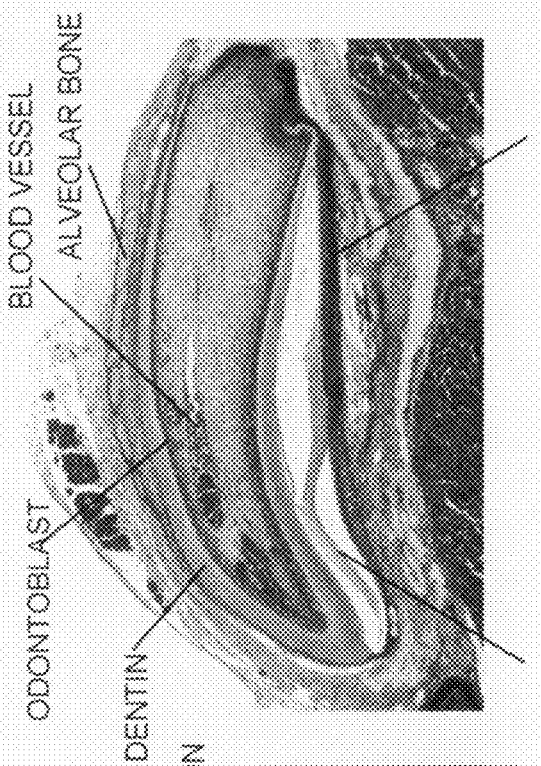
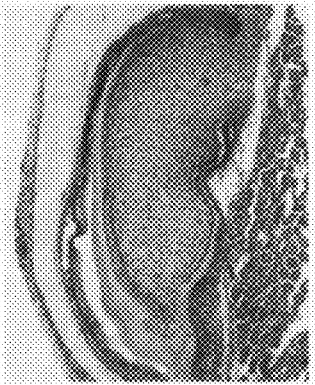
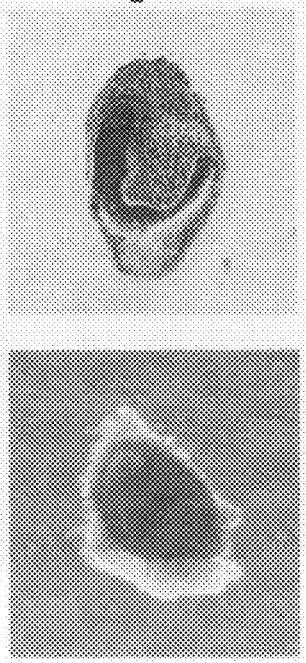

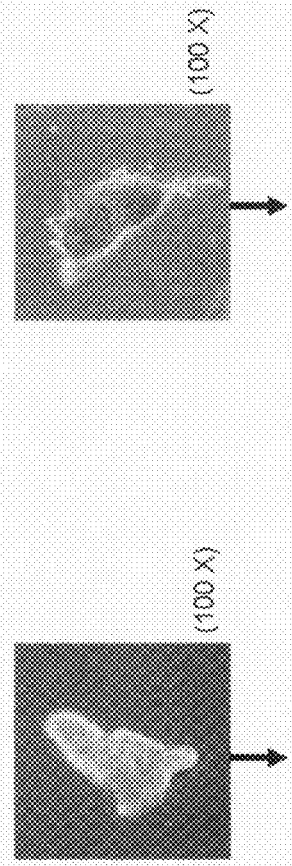
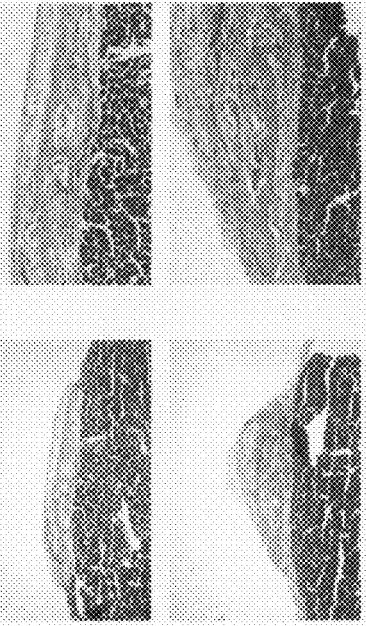
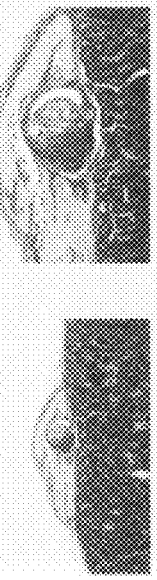
FIG.8

FIG.11
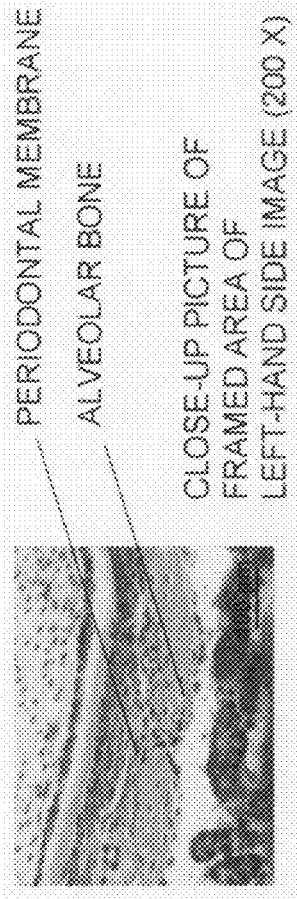
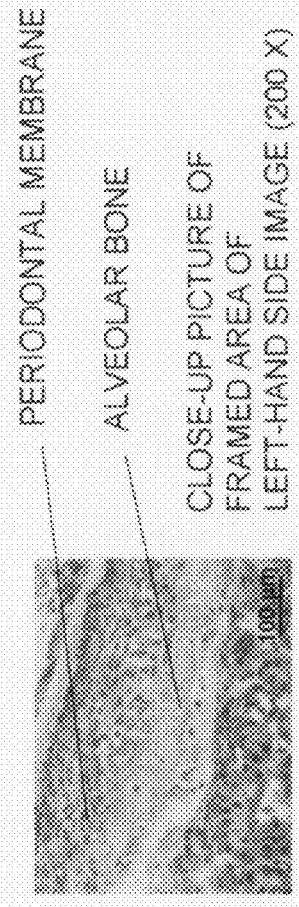
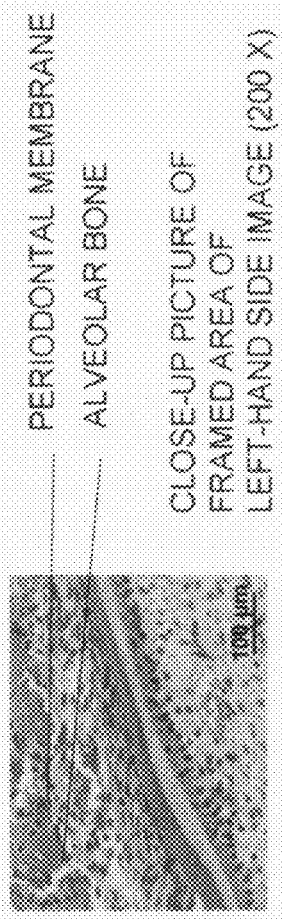

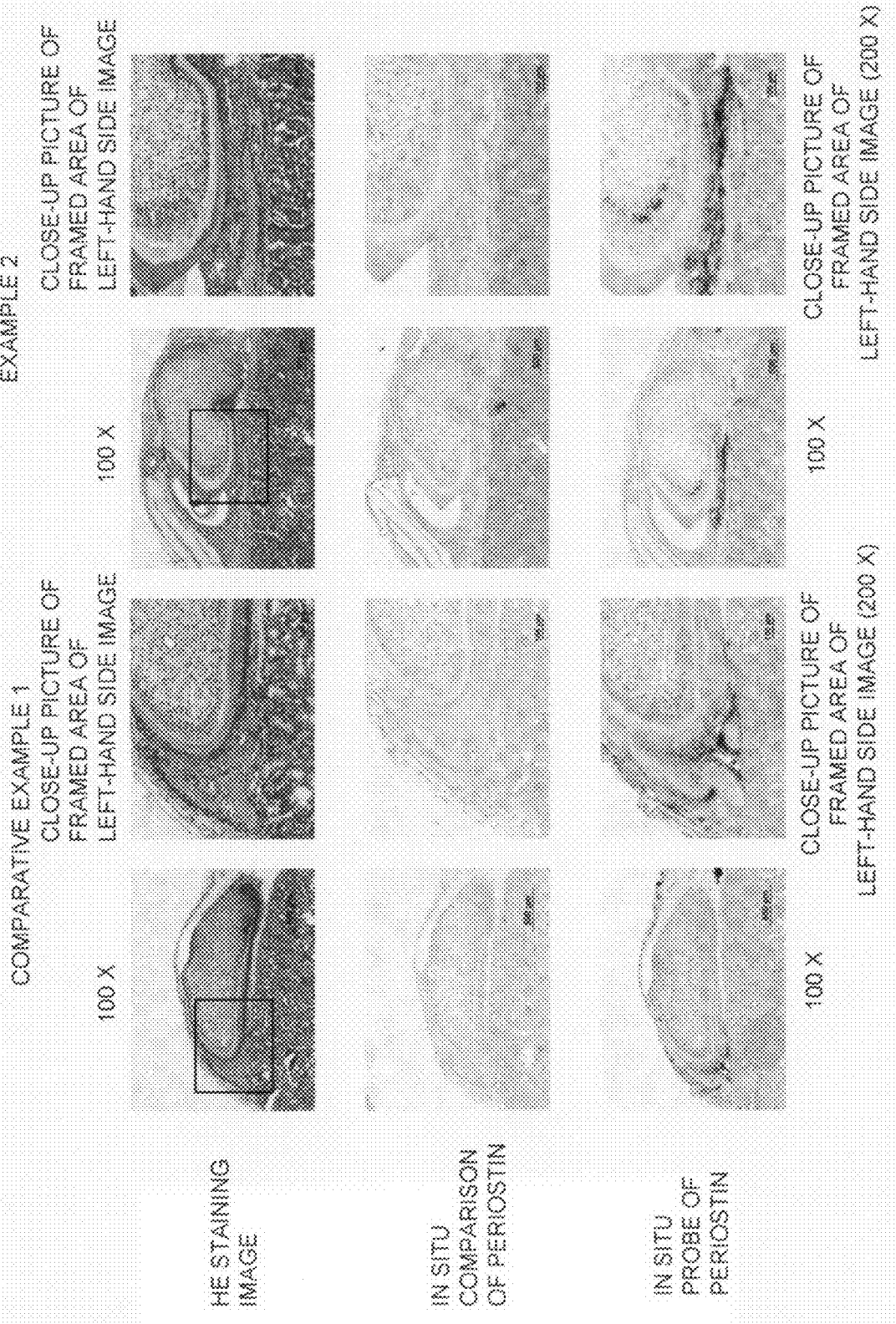

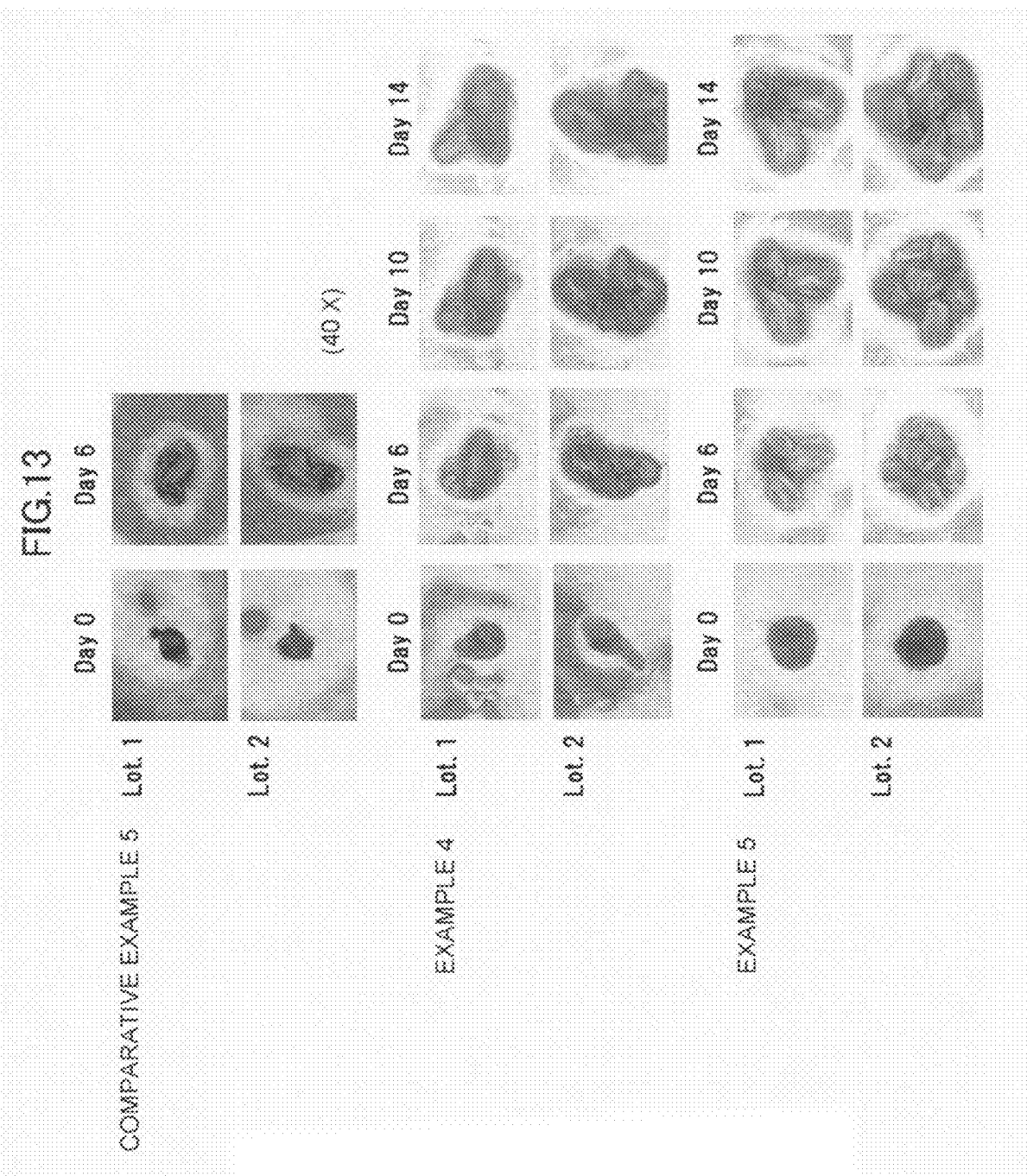

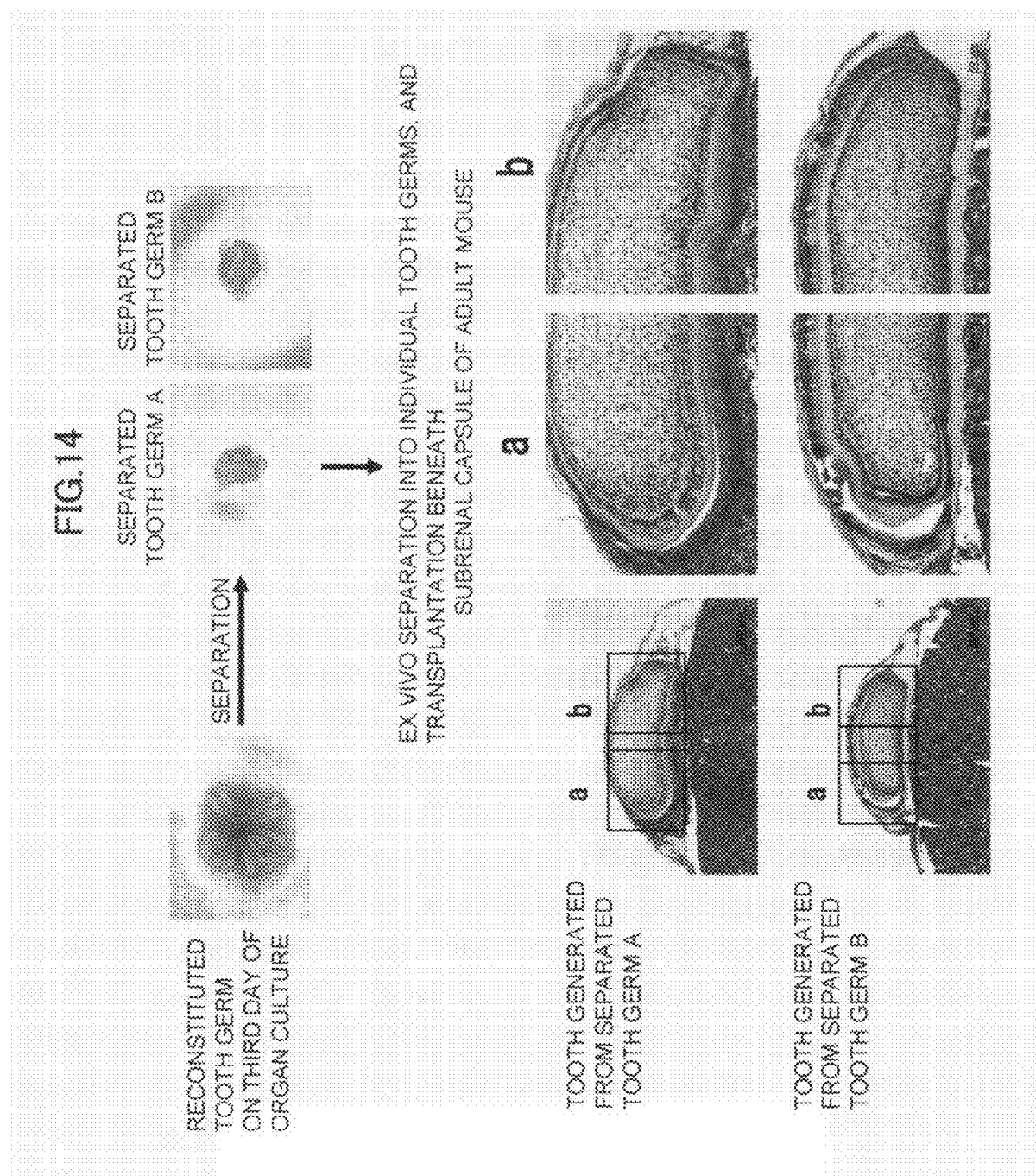

FIG.16
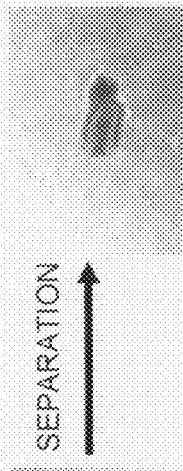
RECONSTITUTED TOOH GERM ON THIRD DAY OF ORGAN CULTURE
SEPARATION
INDIVIDUALLY SEPARATED TOOTH GERM
TRANSPLANTATION INTO HOLE LEFT BY EXTRACTED INCISOR TOOTH IN ORAL CAVITY OF ADULT MOUSE
CLOSE-UP PICTURE OF FRAMED AREA OF LEFT-HAND SIDE IMAGE
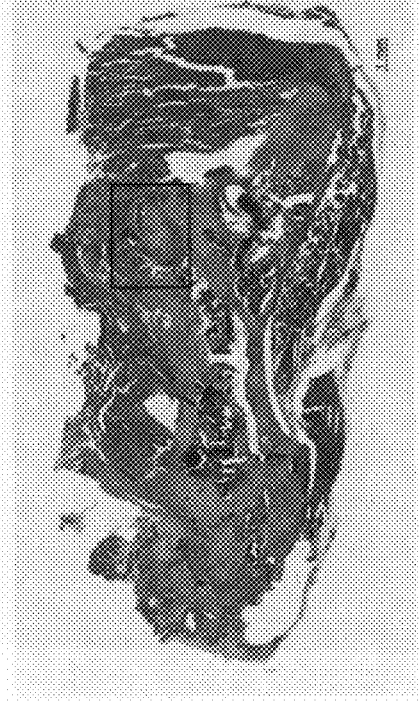
ARROW INDICATES THE GENERATED TOOTH FIG. 17
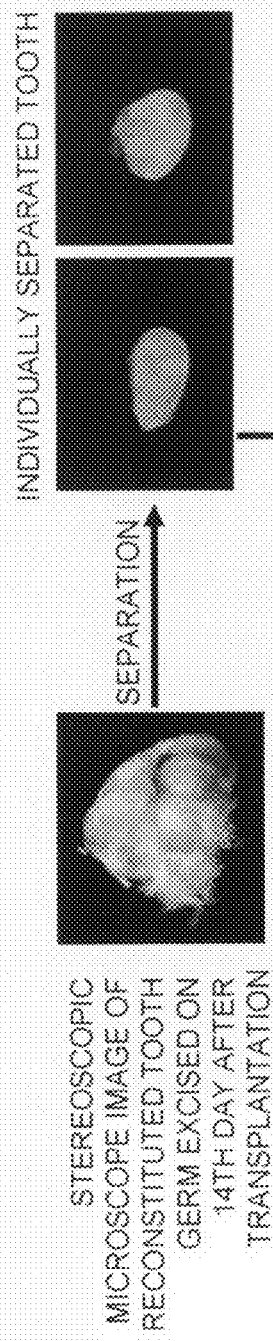
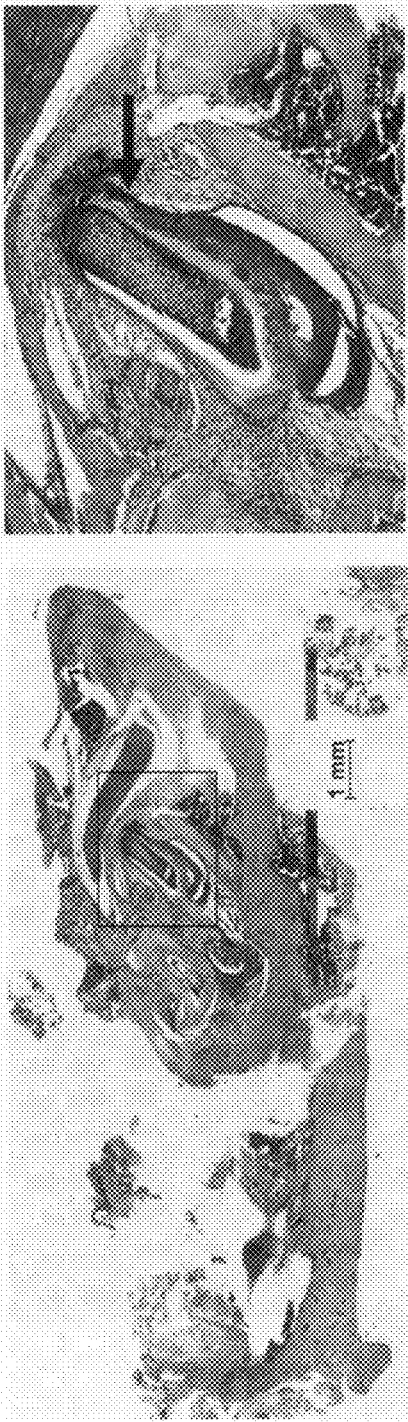

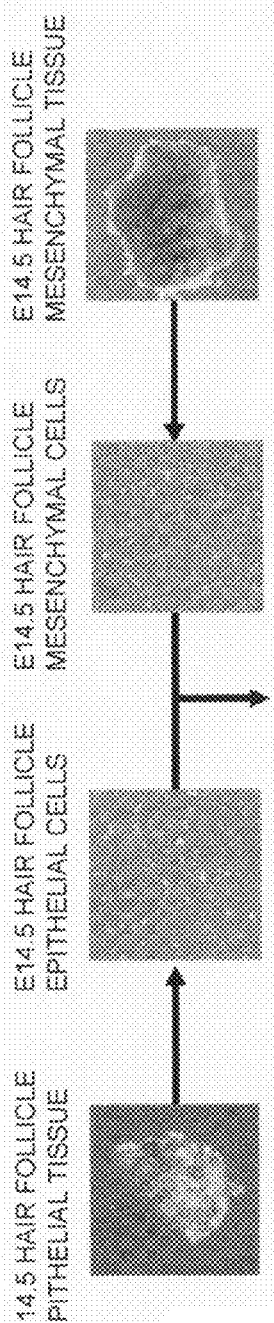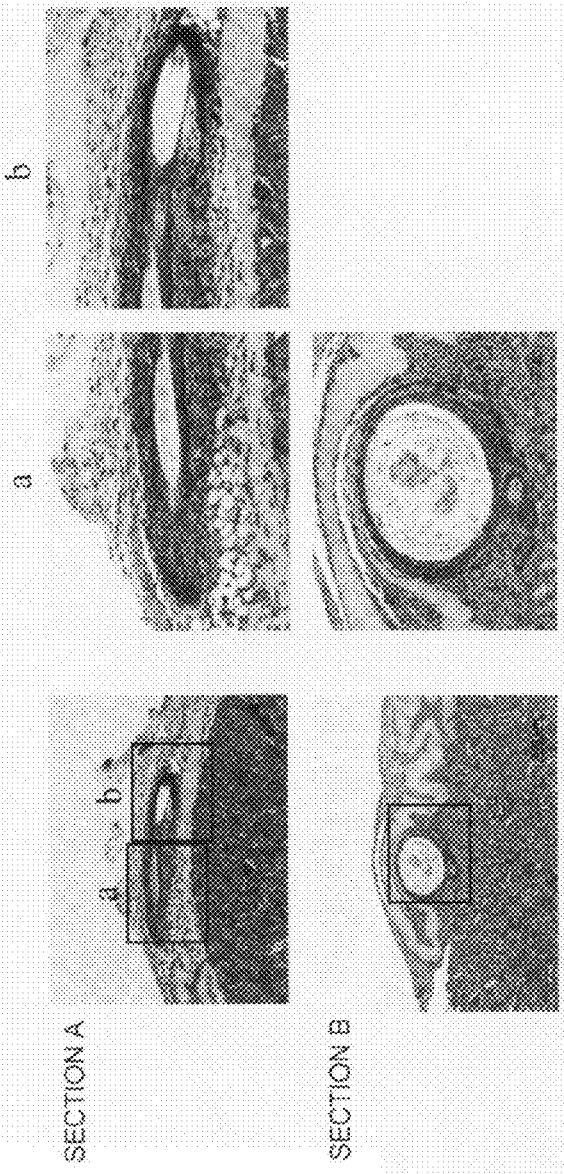
FIG. 18

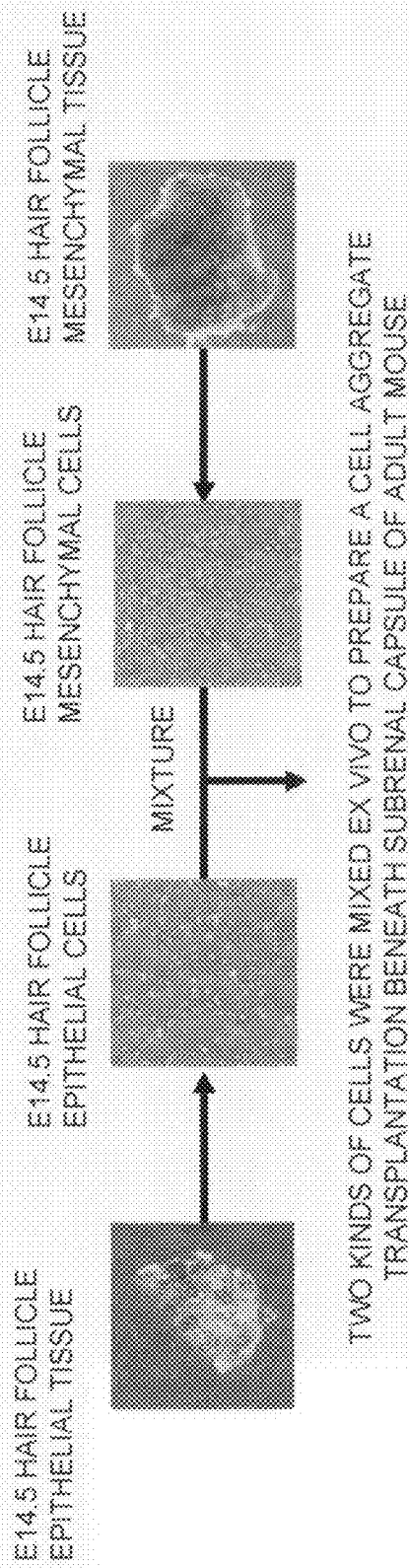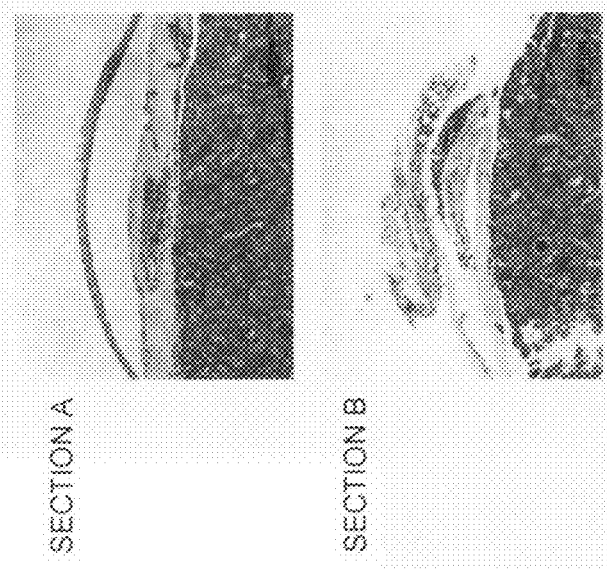
FIG. 20

METHOD OF PRODUCING TOOTH, SET OF TEETH, AND METHOD OF PRODUCING TISSUE

FIELD OF THE INVENTION

The present invention relates to a method of producing a tooth, a set of teeth, and a method of producing tissue and, specifically, to a method of producing a tooth, a set of teeth, and a method of producing tissue using cells.

BACKGROUND ART

The tooth is an organ, which can be lost by dental caries, periodontal diseases or the like, and which has hard tissues such as enamel in the outermost layer and dentin in the inner layer, and further has an odontoblast which forms dentin in the deeper layer of the tooth and dental pulp in the core. Generally, tooth loss today is mainly compensated for by dentures and implants in many cases, as this is thought to have little threat to life. However, there is a growing interest in the development of tooth regenerative technology in view of the significant influence that the presence or absence of teeth has on personal appearance and on the taste of food, and from the perspective of maintaining health and a high quality of life.

Teeth are functional units that are formed by induction during the developmental process of the fetal stage and constructed with plural cell types, and they are thought to be the same as organs or internal organs. Therefore, teeth are not produced by the stem cell system in which cell types are produced from stem cells such as hematopoietic stem cells and mesenchymal stem cells in the adult body, and teeth cannot be regenerated solely by stem cell implantation (stem cell implant therapy) which is currently under development by regenerative medicine. Moreover, while regeneration of teeth by identifying the gene that is specifically expressed in the tooth developmental process and artificially inducing a tooth germ is being considered, tooth regeneration cannot be induced completely simply by identifying the gene.

Therefore, studies have been conducted recently with a central focus on tooth regeneration by transplanting a reconstituted tooth germ obtained by reconstituting a tooth germ using isolated tooth germ cells.

For example, in Non-patent Document 1, it is disclosed that a tooth-like tissue is regenerated by transplanting cells, such as epithelial cells isolated from a tooth germ and mesenchymal dental follicle cells, with a bioabsorbable carrier into an abdominal cavity of a rat.

In Non-patent Document 2, it is described that co-culture by collagen gel is effective as a system in which an epithelium/mesenchymal interaction by subcultured cells can be realized.

As a method of regenerating a tooth germ, it is described, for example, in Patent Document 1, that tooth germ cells are cultured in the presence of physiologically active substances such as fibroblast growth factors and the like. In Patent Document 2, it is proposed that at least one type of cells selected from tooth germ cells and cells which can be differentiated into these tooth germ cells are cultured along with a fibrin-containing carrier, and it is described that a "tooth" having a specific shape is formed by using a fibrin-containing carrier having the desired shape for the tooth germ.

In Patent Documents 3 and 4, a method of forming teeth is disclosed that includes seeding a cell mixture of a tooth germ containing dentin forming mesenchymal cells derived from dental pulp and epithelial cells which contribute to enamel formation, from the mandible of a 6 month-old pig, into a scaffold which is a solidified biodegradable polymer containing a polyglycolic acid/polyacetic acid copolymer; and transplanting it into an animal body. Here, it is described that a "tooth" having a specific shape is formed by using a scaffold having the desired shape for the tooth germ.

Further, in Patent Document 5, a method of tooth regeneration for treating a patient with bone loss or damage is disclosed. According to this method, a bone is formed by seeding mesenchymal cells in a polyglycolic acid mesh carrier and then laminating the carrier with epithelial cells and collagen or wrapping it with an epithelial cell sheet. Further, in Patent Document 5, a carrier is used to construct the shape of a bone.

Non-patent Document 1: *J. Dent. Res.*, 2002, Vol. 81 (10), pp. 695-700

Non-patent Document 2: "Regenerative medicine using teeth and cells derived from a tooth germ and the possibility of the same," *Regenerative Medicine*, Journal of the Japanese Society for Regenerative Medicine, 2005, Vol. 4(1), pp. 79-83

Patent Document 1: Japanese Patent Application Laid-open No. 2004-331557

Patent Document 2: Japanese Patent Application Laid-open No. 2004-357567

Patent Document 3: US Patent Application Publication No. 2002/0119180

Patent Document 4: US Patent Application Publication No. 2004/0219489

Patent Document 5: International Publication (WO) No. 2005/014070

DISCLOSURE OF THE INVENTION

Problems to be Solved by the Invention

However, in order to function as a tissue, it is essential that plural types of cells constituting a tissue are placed in an appropriate relative position (cell placement) and have directionality as a tissue. Tissue, for example, a tooth, is an "internal organ" or "organ" produced by an interaction between epithelial cells derived from a tooth germ and mesenchymal cells derived from cranial neural crest cells during differentiation-developmental processes. It is possible to produce normal teeth by transplanting a tooth germ as it is; however, teeth having the specific cell placement and the directionality of the functional unit that is a tooth cannot be regenerated only by isolating and culturing tooth germ cells constituted by plural types of cells.

Although a tooth germ is reconstructed using cells, cellular factors and the like in the above-mentioned techniques, the specific cell placement and directionality sufficient to express the functions of a tooth, are not regenerated.

Further, it has been difficult to reconstruct tissue having the specific cell placement simply by isolating and culturing plural cells which constitute the tissue.

Therefore, an object of the present invention is to provide a method of producing a tooth having a specific cell placement, a set of tooth prepared by this method, and a method of producing periodontal tissue.

Moreover, another object of the present invention is to provide a method of producing a tissue having a tissue-specific cell placement.

Means for Solving the Problem

A method of producing a tooth of the present invention includes positioning a first cell mass substantially containing only either one of mesenchymal cells or epithelial cells wherein at least one of the mesenchymal cells or epithelial cells is derived from a tooth germ, and a second cell mass substantially containing only the other one of the mesenchymal cells or epithelial cells, inside a support carrier and in contact with each other, and culturing the first and the second cell masses inside the support carrier.

A method of producing periodontal tissue of the present invention includes positioning a first cell mass substantially containing only either one of mesenchymal cells or epithelial cells wherein at least one of the mesenchymal cells or epithelial cells is derived from a tooth germ, and a second cell mass substantially containing only the other one of the mesenchymal cells or epithelial cells, inside a support carrier and in contact with each other, culturing the first and the second cell masses inside the support carrier until a tooth and periodontal tissue contiguous to the tooth are obtained, and isolating the periodontal tissue obtained by the culture.

A set of teeth of the present invention is obtained by positioning a first cell mass substantially containing only either one of mesenchymal cells or epithelial cells wherein at least one of the mesenchymal cells or epithelial cells is derived from a tooth germ, and a second cell mass substantially containing only the other one of the mesenchymal cells or epithelial cells, inside a support carrier and in contact with each other, and culturing the first and the second cell masses inside the support carrier.

In both of the above-mentioned methods or the set of teeth, it is preferable that each of the above-mentioned first cell mass and second cell mass is derived from a tooth germ.

Moreover, each of the above-mentioned first cell mass and second cell mass may be a mass of single cells.

Further, a method of producing tissue of the present invention is a method of producing tissue constructed by interaction between mesenchymal cells and epithelial cells, the method including positioning a first cell mass substantially containing only either one of mesenchymal cells or epithelial cells and a second cell mass substantially containing only the other one of the mesenchymal cells or epithelial cells, inside a support carrier and in contact with each other, and culturing the first and the second cell masses inside the support carrier.

In the above-mentioned method of producing tissue, it is preferable that at least one of the above-mentioned mesenchymal cells and epithelial cells is cells derived from a targeted tissue.

Moreover, the above-mentioned tissue is characterized by being selected from the group consisting of a tooth, a hair, a kidney, a lung and a liver.

In the present invention, since cell masses substantially containing only mesenchymal cells or epithelial cells are positioned inside a support carrier in contact with each other and cultured, each cell mass grows inside the support carrier without being mixed with the cells which constitute the other cell mass, while the state of contact between the masses is maintained. This makes it possible to effectively reproduce the excellent interaction between the mesenchymal cells and the epithelial cells required in formation of the tissue.

As a result, a tissue having the specific cell placement for the targeted tissue can be prepared. Moreover, a tooth or a set of teeth having a specific cell placement, in which there is enamel outside and dentin inside, can be prepared when at least one of the mesenchymal cells and the epithelial cells is derived from a tooth germ.

Effect(s) of the Invention

According to the present invention, a method of producing a tooth having a specific cell placement, a set of teeth prepared by this method, and a method of producing periodontal tissue can be provided.

Furthermore, according to the present invention, a method of producing of tissue having cell placement specific to the tissue can be provided.

BRIEF EXPLANATION OF DRAWINGS

FIG. 3 shows phase contrast images and staining images of normal tooth germ tissues and time course staining images of the tooth produced by the subrenal capsule transplantation of the normal tooth germ, according to Comparative Example 1 of the present invention.

FIG. 8 shows phase contrast images of epithelial tissues derived from a tooth germ and mesenchymal tissues derived from a tooth germ and chromatic figures of the $14^{th}$ day of individual subrenal capsule transplantation of each of the above tissues, according to Comparative Example 2 of the present invention.

FIG. 11 shows staining images of the alveolar bone and periodontal membrane which are periodontal tissues formed around the tooth produced from the reconstituted tooth germ according to Examples 1 to 3 of the present invention.

FIG. 12 shows staining images of detected periostin mRNA specific to a periodontal membrane which is a periodontal tissue formed around the tooth produced from the reconstituted tooth germ according to Example 2 of the present invention (17th day after the transplantation) and Comparative Example 1 (14th day after the transplantation).

FIG. 13 shows phase contrast images and staining images of the tooth produced by organ culture by extending the culture process after preparing the reconstituted tooth germ according to Examples 4 and 5 of the present invention and Comparative Example 5.

FIG. 14 shows phase contrast images of a tooth germ reconstituted by epithelial cells derived from a tooth germ and mesenchymal cells derived from a tooth germ and staining images of the 14th day of the tooth produced by subrenal capsule transplantation of the reconstituted tooth germ, according to Example 6 of the present invention.

FIG. 16 shows staining images of the 14th day after transplantation of an individually separated tooth germ into the oral cavity, according to Example 6 of the present invention.

FIG. 17 shows staining images of the 14th day after transplantation of an individually separated tooth into the oral cavity, according to Example 7 of the present invention.

FIG. 18 shows phase contrast images of a hair follicle reconstituted by epithelial cells derived from hair follicle tissue and mesenchymal cells derived from hair follicle tissue and staining images of the 14th day of the hair produced by subrenal capsule transplantation of the reconstituted hair follicle, according to Example 8 of the present invention.

FIG. 20 shows phase contrast images of a hair follicle reconstituted by epithelial cells derived from hair follicle tissue and mesenchymal cells derived from hair follicle tissue according to Comparative Example 7 of the present invention and staining images of the 14th day of the hair follicle produced by subrenal capsule transplantation of the reconstituted hair follicle.

BEST MODE FOR CARRYING OUT THE INVENTION

Figure 1:
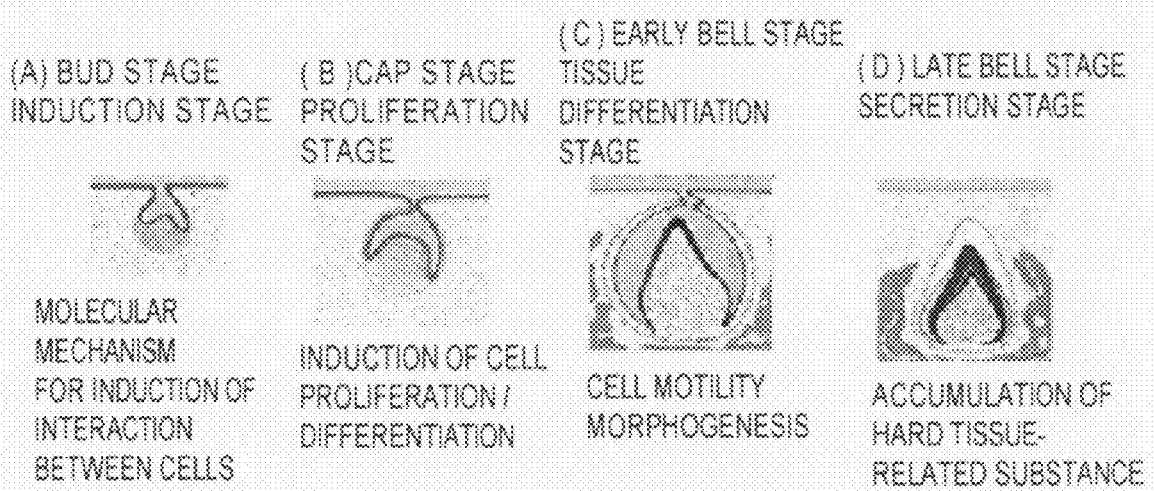
FIG. 1 is a schematic diagram showing formation of the tooth germ.
Figure 2A:
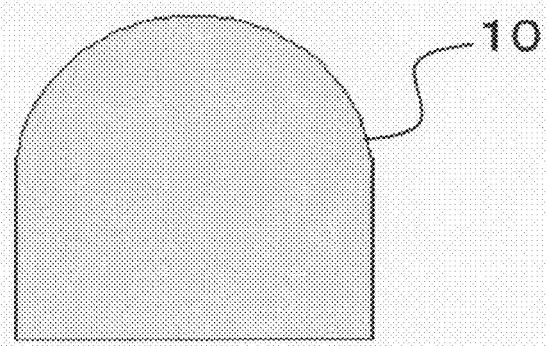
FIG. 2 (A) to (D) are schematic views conceptually showing a procedure for reconstruction of a tooth germ using mesenchymal cells and epithelial cells which are derived from a tooth germ, according to the Examples of the present invention.
Figure 2B:
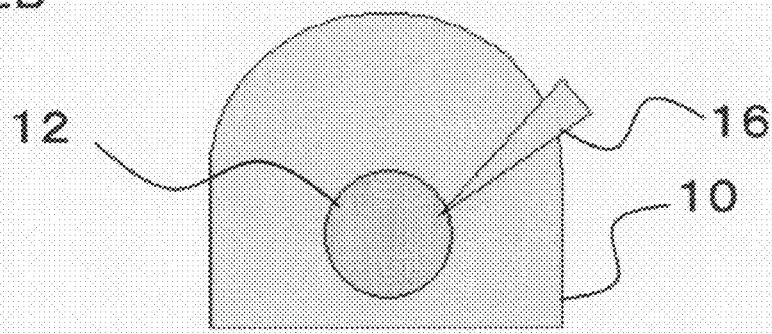
Figure 2C:
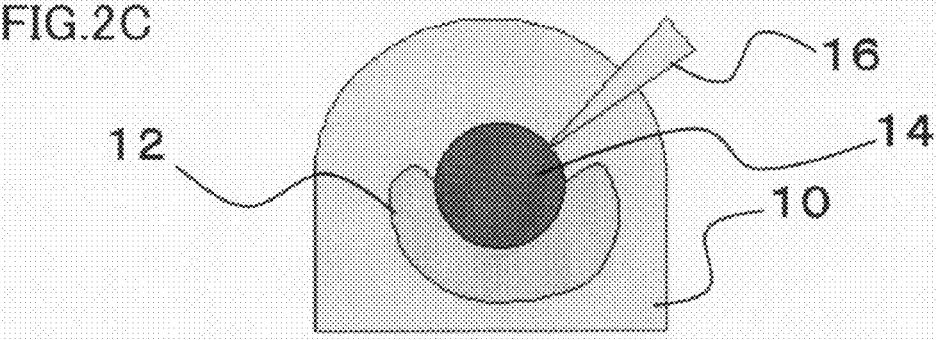
Figure 2D:
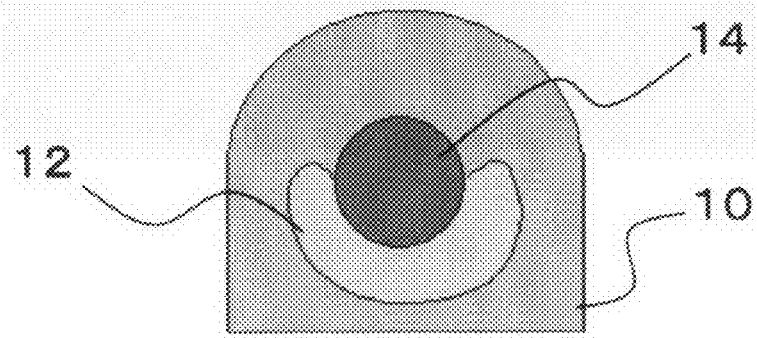

A method of producing a tooth of the present invention includes: positioning a first cell mass substantially containing only either one of mesenchymal cells or epithelial cells in which at least one of the mesenchymal cells or epithelial cells is derived from a tooth germ and a second cell mass substantially containing only the other one of the mesenchymal cells or epithelial cells, inside a support carrier and in contact with each other (placement process); and culturing the above-mentioned first and second cell masses inside the above-mentioned support carrier (culture process).

In the present method of producing a tooth, since the mesenchymal cells and epithelial cells, at least one of the mesenchymal cells or epithelial cells being derived from a tooth germ, are grown as cell masses in a support carrier while in contact with each other, the interaction between the cells can be effectively performed due to the state of close contact therebetween and a tooth having a cell placement specific to teeth, in which there is dentin inside and enamel outside, can be produced.

In the present invention, the term, "tooth" refers to a tissue having a dentin layer inside and an enamel layer outside contiguously, and preferably to a tissue having these layered structures and also a directionality having a crown and root. Those skilled in the art can easily identify dentin and enamel morphologically by tissue staining and the like. Moreover, enamel can be identified by the presence of an ameloblast, and the presence of an ameloblast can be confirmed by the presence of amelogenin. On the other hand, dentin can be identified by the presence of an odontoblast, and the presence of an odontoblast can be confirmed by the presence of dentin sialoprotein. The presence of amelogenin and dentin sialoprotein can be confirmed easily by a well-known method in the art; for example, in situ hybridization, antibody staining or the like.

Further, the directionality of a tooth can be identified by the placement of a crown and root. The crown and root can be confirmed based on the visually observed shape and tissue staining.

In addition, in the present invention, the term "periodontal tissue" refers to an alveolar bone and a periodontal membrane formed mainly in the outer layer of a tooth. Alveolar bone and periodontal membrane can be easily morphologically identified by those skilled in the art by tissue staining or the like.

Further, in the present invention, the term, "mesenchymal cells" refers to cells derived from mesenchymal tissue and "epithelial cells" refers to cells derived from epithelial tissue.

In the present invention, the terms, "tooth germ" and "tooth bud" are expressions used to refer specifically to the tooth germ and tooth bud which are distinguishable from other tissue based on the developmental stage described later. In this case, "tooth germ" refers to an early-stage embryo of a tooth, which is destined to become a tooth in the future, and to tissue from the bud stage to the bell stage in the typical developmental stages of a tooth and, specifically, to tissue at which no accumulation of dentin and enamel is identified, which are the features of tooth as a hard tissue. A "tooth bud" refers to a tissue in terms of the transition of the stages of the "tooth germ" used in the present invention, and to a tissue between the stage where the accumulation of dentin and enamel, which are the features of the hard tissue of tooth, is started, and the stage before the tooth germinates from the gum to manifest the typical functions of the tooth.

A tooth germ, as shown in FIG. 1, develops through each stage of a bud stage, a cap stage, an early bell stage and a late bell stage in the ontogenic process. In the bud stage, epithelial cells invaginate to wrap around mesenchymal cells (see (A) and (B) of FIG. 1), and the epithelial cell portion becomes the outer enamel and the mesenchymal cell portion begins to form dentin internally (see (C) and (D) of FIG. 1) as it moves to the early bell stage and late bell stage. Therefore, a tooth germ is formed by the interaction between epithelial cells and mesenchymal cells.

The mesenchymal cells and epithelial cells in the present invention may be those in the stages from the above-mentioned bud stage to the late bell stage, where a tooth germ is formed or can be formed (hereinafter, simply referred to as a "tooth germ"), and from the viewpoint of the level of immaturity and the homogeneity in the differentiation stages of the cells, it is preferable that they are in the stages from the bud stage to the cap stage.

Moreover, the term, "cell mass" refers to a state in which cells are closely packed and may refer to the condition of tissue or the condition of single cells. In addition, the term, "substantially containing" means that anything other than the target cells are excluded to the greatest possible extent. Since each cell mass may be a tissue itself or a part thereof, or a mass of single cells, either one of the cell masses may be a cell mass constituted by single cells or both of the cell masses may be cell masses constituted by single cells; however, in order to effectively achieve the reconstruction of tissue according to the present invention, it is preferable that both cell masses are constituted by single cells.

Either a first cell mass or a second cell mass may be epithelial cells or mesenchymal cells and the number of cells constituting the cell mass may vary depending on animal species, and on the type, hardness and size of the support carrier, but it may generally be from $10^1$ to $10^8$ cells per cell mass, and preferably from $10^3$ to $10^8$ cells per cell mass.

In the positioning process, a first cell mass and a second cell mass are positioned inside a support carrier in contact with each other.

In the positioning process of the production method of the present invention, since the above-mentioned first and second cell masses are positioned inside a support carrier which can maintain the state of contact of the cells, cells constituting each cell mass do not mix with the cells constituting the other cell mass. Thus, in the positioning process, each cell mass is positioned without being mixed with the other, and a boundary surface is formed between the cell masses. Such an positioning mode is suitably expressed as "compartmentalization" in the present specification.

In this case, a first cell mass and a second cell mass are prepared in independent preparation processes (first cell preparation process and second cell preparation process) so that each of cell mass may be substantially constituted by mesenchymal cells or epithelial cells.

At least either one of mesenchymal cells or epithelial cells used in the present production method may be derived from a tooth germ in order to reproduce in vivo cell placement to form a tooth having a specific structure and directionality; however, in order to ensure tooth production, most preferably both of the mesenchymal cells and the epithelial cells are derived from a tooth germ.

Examples of mesenchymal cells derived from other than a tooth germ include cells derived from other mesenchymal tissues in vivo; preferably, bone marrow cells including no blood cells, or mesenchymal stem cells; more preferably, mesenchymal cells in the oral cavity and bone marrow cells inside the jaw bone, and mesenchymal cells derived from cranial neural crest cells; and mesenchymal precursor cells, which can generate the above-mentioned mesenchymal cells, stem cells thereof, and the like.

Further, examples of epithelial cells derived from tissues other than a tooth germ include cells derived from other epithelial tissues in vivo; preferably, epithelial cells of skin, mucous membrane or gum in the oral cavity; and more preferably, immature epithelial precursor cells which can produce differentiated epithelial cells, for example, keratinized or parakeratinized epithelial cells of the skin and mucous membrane; for example, non-keratinized epithelial cells and stem cells thereof, and the like.

The tooth germ and other tissues may be collected from the jaw bone of various animals such as primate mammals such as humans and monkeys; ungulates such as pigs, cows and horses; rodent small mammals such as mice, rats, and rabbits. In the collection of the tooth germ and tissue, conditions generally used in the collection of tissue may be applied without modification, and the tooth germ and tissue may be extracted in sterile conditions and stored in an appropriate preservative solution. Further, examples of a human tooth germ include a fetal tooth germ as well as the third molar, or so-called wisdom tooth, but it is preferable to use the tooth germ of a wisdom tooth from the standpoint of the use of autogenous tissues.

The preparation of mesenchymal cells and epithelial cells from such a tooth germ is started by separating a tooth germ, which has been isolated from the surrounding tissue, into a tooth germ mesenchymal tissue and a tooth germ epithelial tissue according to the respective shapes thereof. The tooth germ tissues can be easily separated by cutting or tearing using dissecting scissors, tweezers or the like, since it is possible to identify the tooth germ tissues structurally under a microscope. Further, the separation of tooth germ mesenchymal tissue and tooth germ epithelial tissue from the tooth germ can be easily done by cutting or tearing using injection needles, tungsten needles, tweezers or the like, according to the respective shapes thereof.

Preferably, enzymes may be used to easily separate tooth germ cells from the surrounding tissue and/or to separate an epithelial tissue and a mesenchymal tissue from a tooth germ tissue. Examples of the enzymes used in such applications include dispase, collagenase, trypsin and the like.

Mesenchymal cells and epithelial cells may be prepared in a single cell state from a mesenchymal tissue and an epithelial tissue, respectively. In the preparation process, enzymes may be used to make the cells easily dispersible as single cells. Examples of such enzymes include dispase, collagenase, trypsin and the like. In this case, for separation of the epithelial cells from the epithelial tissue, it is preferable to perform trypsin treatment and DNase treatment after collagenase treatment. On the other hand, for the separation of the mesenchymal cells from the mesenchymal tissue, it is preferable to perform collagenase treatment and trypsin treatment simultaneously and ultimately to perform DNase treatment. In this case, the DNase treatment is performed in order to prevent a decrease in the amount of recovered cells resulting from cell aggregation caused by DNA released into the solution when the cell membrane is lysed, after some of the cells are damaged by the enzyme treatments.

In addition, the mesenchymal cells and epithelial cells may be those which have been subjected to preliminary culture prior to the positioning process in order to obtain a sufficiently large number of each kind of the cells. In the culture of mesenchymal cells and epithelial cells, the usual conditions, such as temperature, used in the culture of animal cells can be applied without modification.

As a medium used in the culture, a medium generally used for animal cell culture, such as Dulbecco's Modified Eagle Medium (DMEM), can be used. Serum may be added to promote cell proliferation, or as alternatives to the serum, cellular growth factors such as FGF, EGF, PDGF and the like or well-known serum components such as transferin may be added. In addition, when serum is added, the concentration of the serum may be changed appropriately depending on the culture conditions, but it can usually be 10%. For cell culture, the culture conditions generally used in culture, such as of culture in an incubator in 5% $CO_2$ concentration at 37° C., may be applied. Moreover, antibiotics such as streptomycin may be added as appropriate.

As a support carrier used in the present invention, a support carrier in which cells can be cultured may be used, and a mixture with the above-mentioned culture medium is preferable. Examples of such support carriers include collagen, fibrin, laminin, an extra-cellular matrix mixture, polyglycolic acid (PGA), polylactic acid (PLA), lactic acid/glycolic acid copolymer (PLGA), Cellmatrix (trade name), Mebiol Gel (trade name), and Matrigel (trade name). These support carriers may be of a hardness that can virtually maintain the approximate location at which the cells are positioned inside thereof, and examples thereof include gel type, fiber type, and solid type carriers. In this case, the level of hardness that can maintain the location of the cells may be the level of hardness generally applied in three-dimensional culture; in other words, a level of hardness that does not inhibit hypertrophy of the cells due to proliferation while maintaining the positioning of the cells, and the level of hardness is easily determined. For example, in the case of collagen, use at a final concentration of 2.4 mg/ml provides an appropriate level of hardness.

In addition, in this case, the support carrier may be of a thickness sufficient for the first and second cell masses to grow inside the carrier and is set appropriately based on the size of the targeted tissues.

Moreover, the support carrier may be one that can maintain the state of contact between the cells. The "state of contact" as referred to herein is preferably a high density state in order to ensure cell interaction within each cell mass or between the cell masses.

A high density state refers to a density similar to that at the time when the tissue is constituted such as, in the case of the cell masses, $5 \times 10^7$ to $1 \times 10^9$/ml at the time of cell placement, preferably $1 \times 10^8$ to $1 \times 10^9$/ml to ensure cell interaction without sacrificing the cell activity, and most preferably $2 \times 10^8$ to $8 \times 10^8$/ml. In order to prepare a cell mass at such a cell density, it is preferable to aggregate cells centrifugally and have these precipitated, since this conveniently enables high density without sacrificing the cell activity. The centrifugation may be performed at a revolution speed equivalent to a centrifugal force of 300 to 1200×g, which will not preclude cell survival, and preferably 500 to 1000×g, for 3 to 10 minutes. Centrifugation at lower than 300×g may lead to insufficient cell precipitation and the cell density may become low, while centrifugation at higher than 1200×g may lead to cell damage and, therefore, neither of these cases is preferable.

When high density cells are prepared by centrifugation, centrifugation is generally performed after preparing a suspension of single cells in containers such as tubes used for cell centrifugation, and the supernatant is removed to the greatest extent possible, leaving cells as the precipitate. It is preferable that the containers such as tubes are silicon-coated from the standpoint of completely removing the supernatant.

When precipitates are prepared by centrifugation, the precipitates may be directly positioned inside the support carrier. Here, components other than the targeted cells (for example, a culture solution, a buffer solution, the support carrier and the like) are preferably equal to or less in volume than the cells, and most preferably the components other than the targeted cells are excluded. In such a high density cell mass, cells are in close contact with each other and the interaction between the cells may be achieved effectively.

When used in a tissue state, it is preferable to remove components other than the target cells, such as connective tissues, by performing an enzyme treatment or the like. When there are many components other than the target cells, for example, when the volume of the other components is equal to or more than that of the cells, the interaction between the cells may not be achieved sufficiently, and this is not preferable.

Moreover, it is more preferable when a first cell mass and a second cell mass are in very close contact, and it is especially preferable to position the second cell mass so as to press against the first cell mass. Furthermore, encompassing the surroundings of the first cell mass and the second cell mass with a culture solution or solid which does not inhibit oxygen permeation is also effective in making the contact between the cell masses closer, and it is also preferable to add and position a cell suspension at high density into a solution with a different viscosity to solidify the solution as is, since the cell contact can be easily maintained thereby. Here, it is preferable to position the enamel knot of a tooth germ epithelial tissue in contact with the first cell mass when the first cell mass is single cell mass of tooth germ mesenchymal cells and the second cell mass is a tooth germ epithelial tissue, but the invention is not limited to this.

When the support carrier is in a gel state, a solution state or the like, the solidification process by which a support carrier is solidified may be arranged so as to follow after the positioning process. Cells positioned inside the support carrier may be fixed inside the support carrier by the solidification process. For solidification of the support carrier, conditions generally used for the solidification of support carriers may be applied without modification. For example, when solidifiable compounds such as collagen are used for the support carrier, they can be solidified under generally applied conditions by, for example, being held still for several minutes to several tens of minutes at the culture temperature. In this way, binding between cells inside the support carrier can be fixed and robust.

In the culture process of the production method of the present invention, a first cell mass and a second cell mass are cultured inside the support carrier. In this culture process, the interaction between the cells is effectively performed by the first cell mass and the second cell mass which are in close contact with each other, to reconstitute a tissue, namely, a tooth.

The culture process may be performed such that the state of contact between the first cell mass and the second cell mass is maintained by the support carrier and the process may be culture in a support carrier which simply has first and second cell masses, or culture in the presence of other cells of animals.

The culture period varies depending on the number of cells positioned in the support carrier and the state of the cell mass and, further, on the conditions under which the culture process is performed; however, it typically takes from 1 to 300 days, and preferably from 1 to 120 days, to form a tooth having enamel outside and dentin inside, and preferably 1 to 60 days from the standpoint of providing quick results. Further, it typically takes 1 to 300 days, and preferably 1 to 60 days, to form a tooth having periodontal tissue.

When culture is performed only in the support carrier, culture can be performed under the general conditions used for culture of animal cells. Here, conditions for culture generally used for animal cells can be applied without modification and the above-mentioned conditions can be applied without modification. Further, serum derived from mammals and various cellular factors which are known to be effective in proliferation and differentiation of these cells, may be added to the culture. Examples of these cellular factors include FGF and BMR.

In addition, it is preferable to use organ culture from the standpoint of gas exchange and nutrient supply for tissues and cell masses. In organ culture, generally, culture is performed by floating a porous membrane on a culture medium suitable for proliferation of animal cells and placing the cell masses embedded in a support carrier on the membrane. The porous membrane used herein is preferably a membrane having many pores of 0.3 to 5 μm in diameter and specific examples include a Cell Culture Insert (trade name) and an Isopore Filter (trade name).

Performing the culture in the presence of other cells of animals is preferable because a tooth having a specific cell placement can be formed in the early stage in response to the actions of various cytokines and the like from animal cells. Such culture in the presence of other cells of animals may be performed ex vivo using isolated cells and cultured cells.

Furthermore, it is especially preferable to perform culture in vivo by transplanting the support carrier having first and second cell masses into a living body, since a tooth and/or a periodontal tissue can be formed in an early stage. In this case, the first and the second cell masses are transplanted with the support carrier into the living body.

Animals which can be used for this application preferably include mammals, for example, humans, pigs, mice and the like, and more preferably animals derived from the same species as that of the tooth germ tissue. When a human tooth germ tissue is transplanted, it is preferable to use a human or mammals other than humans which have been altered to be immunodeficient. As for sites in a living body suitable for such in vivo growth, subrenal capsule, mesentery, and subcutaneous transplantation are preferable for the transplantation in order to generate organs or tissues of the animal cells as normally as possible.

The growth period according to the transplantation varies depending on the size of the explant at the time of transplantation and the size of the tooth to be produced, but is typically 3 to 400 days. For example, the subrenal capsule transplantation period is preferably 7 to 60 days from the standpoint of the tooth regeneration and the size of the tooth to be produced at the site of the transplantation, although it varies depending on the size of explant to be transplanted and the size of the tooth to be regenerated.

Ex vivo culture (preculture) may be performed prior to transplantation to the living body. The preculture is preferable since the bonds between cells and the bond between the first and the second cell masses can be made stronger to make the interaction between cells stronger. As a result, the overall growth period can be shortened.

The preculture period may be short or long. It is desirable to have a longer period, for example, 3 days or more, and preferably 7 days or more, since a tooth bud can be produced from a tooth germ and thus the period until a tooth is formed after the transplantation can be shortened. The period of preculture of, for example, organ culture to transplant beneath a subrenal capsule, is preferably 1 to 7 days in order to effectively regenerate a tooth.

A tooth produced according to the production method of the present invention has a tooth-specific cell placement (structure) having dentin inside and enamel outside, and preferably has directionality, that is, has a tip (crown) and a root of a tooth. By having at least this specific cell placement, and by preferably having directionality in addition to the cell placement, the functions of a tooth can be manifested. Therefore, such a tooth can be widely used extensively as a tooth replacement. Particularly when the mesenchymal cells and epithelial cells derived from an autogenous tooth germ are used, problems caused by rejection can be avoided. Generally, it is also possible to avoid problems caused by rejection when the cells are derived from the tooth germ of another human having a matching transplantation antigen.

Further, in the present invention it is possible to form periodontal tissue in addition to a tooth itself, such as alveolar bone and periodontal membrane, which support and stabilize teeth on the jaw bone, by extending the culture period. As a result, a practicable tooth can be provided after the transplantation.

That is, the method of producing periodontal tissue of the present invention is characterized by containing the above-mentioned culture process as a step to culturing the above-mentioned first and second cell masses inside a support carrier until a tooth and a periodontal tissue contiguous to the tooth can be obtained (culture process), and further containing a step to isolate the periodontal tissue obtained by the above-mentioned culture.

In this method, a periodontal tissue can be formed contiguously to the tooth by extending the culture period until the periodontal tissue is obtained, and periodontal tissue can be obtained in isolation by separating it from the tooth. Isolation of the periodontal tissue may be performed according to any method, in which the periodontal tissue formed during the culture process can be separated from a tooth, for example, separation by tweezers or the like, partial digestion by enzymes, or the like.

In addition, anything described in the above-mentioned method of producing a tooth can be applied to the present method of producing a periodontal tissue as long as the culture period is not limited.

The tooth and periodontal tissue obtained by the above-mentioned method of producing a tooth and method of producing periodontal tissue of the present invention can be used as an effective research tool for producing tissue related to teeth in the future since, in addition to use as an explant, they can be applied to studies investigating the developmental processes of teeth.

Moreover, when the tooth or periodontal tissue obtained is used as an explant, the culture process according to the production method is preferably performed in organ culture in which there is no contact with other cells of animals and the entire procedure can be processed in vitro.

A set of teeth of the present invention is a set of teeth having a tooth-specific cell placement obtained by the above-mentioned method of producing a tooth.

Since such a set of teeth is constituted by plural teeth having a tooth-specific cell placement, each individual tooth can be separated from the set of teeth and used as an explant of a single tooth as described below. Thus, in the method of producing a tooth of the present invention, when plural teeth are produced simultaneously, the teeth can be provided as a set of teeth constituted by plural teeth. As a result, teeth for explants can be efficiently produced.

The set of teeth can be easily obtained by applying the above-mentioned method of producing a tooth without modification. In particular, in the above-mentioned first and second cell preparation processes, each of a first and a second cell mass is separately prepared and then positioned inside a support carrier in contact with each other in the positioning process and, therefore, plural teeth can easily be formed from a cell group which normally forms only a single tooth.

In the method of producing a set of teeth, it is preferable that both of a first and a second cell mass are constituted by single cells in order to facilitate the reinduction of tooth germs to produce plural teeth. In addition, the culture process may be either organ culture or subrenal capsule culture as mentioned above, and when the obtained tooth is used as an explant, it is preferable to perform organ culture in which there is no contact with other cells of animals and the entire procedure can be processed in vitro.

Furthermore, a tooth transplantation method is included in the present invention. This transplantation method includes: a process to obtain the above-mentioned set of teeth; a process in which each tooth is separated from a set of teeth; and a process in which a separated tooth is aligned to have the same directionality as other teeth at the transplantation site, and transplanted.

Thereby, plural teeth having a specific cell placement and directionality can be obtained simultaneously and tooth transplantation can be performed efficiently.

The tooth according to the present invention can be applied to treatments or procedures for tooth loss caused by various symptoms accompanied by loss of or damage to teeth: for example, dental caries, marginal periodontitis (alveolar pyorrhea), and periodontal diseases, tooth breakage or avulsion caused by accidents, and the like.

In other words, a treatment method of the present invention includes transplantation of the tooth and/or periodontal tissue obtained by the production method of the present invention into the site of tooth loss and/or damage. Thereby, the above-mentioned symptoms at the site of tooth loss and/or damage can be treated and/or alleviated.

Another treatment method of the present invention includes carrying out only the culture process of the present invention, or carrying out the positioning process and culture process at the site of tooth loss and/or damage. In this case, the surrounding tissue at the site of tooth loss and/or damage itself may be applied as a support carrier in addition to the support carriers mentioned above. Thus, the site of tooth loss and/or damage can be treated faster by cytokine and the like from the surrounding tissues in the living body.

In the present invention, since tissue can be effectively reconstituted by an interaction between mesenchymal cells and epithelial cells, a method of producing tissue which is constructed by an interaction between mesenchymal cells and epithelial cells can also be provided.

In other words, the method of producing a tissue of the present invention is a method of producing tissue constructed by an interaction between mesenchymal cells and epithelial cells, and includes: positioning a first cell mass substantially containing only either one of mesenchymal cells or epithelial cells and a second cell mass substantially containing only the other of the mesenchymal cells or epithelial cells inside a support carrier in contact with each other; and culturing the above-mentioned first and second cell masses inside the above-mentioned support carrier.

In addition, items described in the above-mentioned method of producing a tooth may be similarly applied to the present method of producing tissue, unless otherwise noted.

As tissues produced by the present method of producing tissue, those constructed by the interaction between mesenchymal cells and epithelial cells are pertinent, and examples of these include a hair, kidney, lung, liver or the like in addition to the tooth mentioned above, and may include the entire tissue or a part thereof.

In this case, it is preferable that at least one of the mesenchymal cells and epithelial cells is derived from the target tissue. In this way, a tissue can be easily formed by using cells which have already been directed to the target tissue. Moreover, in order to produce a targeted tissue more reliably, it is most preferable that both of the mesenchymal cells and epithelial cells are derived from the target tissue.

Examples of tissues used to prepare a cell mass respectively constituted by mesenchymal cells or epithelial cells include: in the case of a tooth, a tooth germ and dental pulp cells, periodontal membrane cells, and epithelial/mesenchymal cells in the oral cavity; in the case of hair, a primordial hair follicle in the developmental process and a hair follicle tissue of an adult; in the case of a kidney, a primordial kidney in the developmental process and a kidney tissue of an adult; in the case of a lung, a primordial lung in the developmental process and a lung tissue of an adult; and in the case of a liver, a primordial liver in the developmental process and a liver tissue of an adult.

In order to prepare each cell mass from these tissues, a first and a second cell mass may be prepared as described above by separating mesenchymal cells and epithelial cells from a tissue, positioning them inside a support carrier, and culturing and/or transplanting as described above.

In this way, as with the above-mentioned tooth, a tissue having a specific cell placement for the targeted tissue can be obtained.

The followings are explanations of Examples of the present invention, but the present invention is not limited to these. "%" as used in Examples is based on weight (mass), unless otherwise noted.

EXAMPLES

Examples 1 to 3 and Comparative Examples 1 to 4

(1) Preparation of Tooth Germ Epithelial Cells and Tooth Germ Mesenchymal Cells

A tooth germ was reconstructed to form a tooth. Mice were used as the model for this experiment.

A mandibular incisor tooth germ tissue was excised from an embryo, having an embryonic age of 14.5 days, of a C57BL/6N mouse (purchased from CLEA Japan, Inc.) or a C57BL/6-TgN (act-EGFP) OsbC14-Y01-FM131 (GFP mouse: RIKEN Bioresource Center) which is a Green Fluorescence Protein (EGFP) transgenic mouse, by the conventional method under a microscope. The mandibular incisor tooth germ tissue was washed with a phosphate buffer solution (PBS (−)) containing neither $Ca^{2+}$ nor $Mg^{2+}$, treated with an enzyme solution, in which Dispase II (Roche, Mannheim, Germany) was added to the PBS (−) at a final concentration of 1.2 U/ml, at room temperature for 12.5 minutes, and then washed three times with DMEM (Sigma, St. Louis, Mo.) to which 10% of FCS (JRH Biosciences, Lenexa, Kans.) had been added. Furthermore, a DNase I solution (Takara, Shiga, Japan) was added to make the final concentration 70 U/ml and the tooth germ tissue dispersed, and tooth germ epithelial tissues and tooth germ mesenchymal tissues were surgically separated using a 25 G injection needle (Terumo, Tokyo, Japan).

For tooth germ epithelial cells, the tooth germ epithelial tissue obtained above was washed three times with PBS (−), and treated twice with an enzyme solution, in which Collagenase I (Worthington, Lakewood, N.J.) at a final concentration of 100 U/ml was dissolved in the PBS (−), at 37° C. for 20 minutes. The cells precipitated and retrieved by centrifugation were further treated with 0.25% Trypsin (Sigma)-PBS (−) at 37° C. for 5 minutes. After washing the cells three times with DMEM supplemented by 10% FCS, a DNase I solution at a final concentration of 70 U/ml was added to the cells, and single tooth germ epithelial cells were obtained by pipetting.

On the other hand, for tooth germ mesenchymal cells, the tooth germ mesenchymal tissue was washed three times with PBS (−) and treated with PBS (−) containing 0.25% Trypsin (Sigma) and 50 U/ml of Collagenase I (Worthington). 70 U/ml of DNase I (Takara) was added and single tooth germ mesenchymal cells were obtained by pipetting.

(2) Preparation of Reconstituted Tooth Germ

Next, a tooth germ was reconstructed using the tooth germ epithelial cells and tooth germ mesenchymal cells prepared as above.

Tooth germ epithelial cells or tooth germ mesenchymal cells suspended with DMEM (Sigma) supplemented by 10% FCS (JRH Biosciences), were added to a silicon grease coated 1.5 mL microtube (Eppendorf, Hamburg, Germany), and the cells were retrieved as precipitates by centrifugation (580×g). The supernatant of the culture solution after centrifugation was removed to the greatest extent possible, centrifugation was conducted again, and the culture solution remaining around cell precipitates was completely removed using a GELoader Tip 0.5 to 20 μL (Eppendorf) while being observed under a stereomicroscope to prepare cells to use for generating a reconstituted tooth germ.

30 μL of Cellmatrix type I-A (Nitta Gelatin, Osaka, Japan) prepared with the above-mentioned culture solution at a concentration of 2.4 mg/ml was dropped on a silicon grease coated Petri dish to generate a drop (gel drop) of collagen solution. 0.2 to 0.3 μL of the precipitates from centrifugation of the above-mentioned tooth germ epithelial cells or tooth germ mesenchymal cells were applied to this solution using a pipette tip (Quality Scientific Plastics) of 0.1 to 10 μL to generate cell aggregates as cell masses.

This will be explained with reference to FIG. 2.

Cell aggregate 12, which was first placed inside gel drop 10 using pipette tip 16, configures a sphere inside the gel drop 10 (see FIG. 2 (B)). When another cell aggregate 14 is then inserted, the spherical cell aggregate 12 is crushed and envelops the cell aggregate 14 in many cases (see FIG. 2 (C)). Then, by solidifying the gel drop 10, the bonds between cells are strengthened.

In the present Example, a cell aggregate containing single cells of the epithelial cells or mesenchymal cells, and a partial tissue containing epithelial cells and a partial tissue containing mesenchymal cells of a tooth germ were prepared, respectively, as cell masses and used.

In the present Example, when combining the reconstituted tooth germs obtained from a cell aggregate and a tissue (Examples 1 and 2), after transferring the partial tissue containing epithelial cells or mesenchymal cells into a gel drop, a boundary surface of the tooth germ of each tissue was placed in close contact with a cell aggregate generated from tooth germ epithelial cells or mesenchymal cells using a tungsten needle to generate a reconstituted tooth germ.

Further, for the reconstituted tooth germ (Example 3) using tooth germ epithelial cells and tooth germ mesenchymal cells which were made as single cells, a cell aggregate was prepared by applying the tooth germ epithelial cells in a similar way to the above so as to contact with the cell aggregate of the tooth germ mesenchymal cells prepared in advance, and a reconstituted tooth germ was prepared such that both would be in close contact with each other.

A reconstituted tooth germ prepared inside a gel drop was set still in a $CO_2$ incubator for 10 minutes to solidify the Cellmatrix type I-A (Nitta Gelatin), and a cell aggregate along with the surrounding gel as a support carrier, were transferred onto a membrane of a cell culture insert in a culture vessel which was arranged such that the cell culture insert (PET membrane with a pore size of 0.4 microns; BD, Franklin Lakes, N.J.) was in contact with DMEM (Sigma) supplemented by 10% FCS (JRH), and organ cultured for 18 to 24 hours. After the organ culture, the tooth generation was analyzed by promoting ectopic tooth generation after transplanting the explant along with the surrounding gel beneath a subrenal capsule of an 8 week-old C57BL/6 mouse, or by continuing the organ culture on the cell culture insert.

As comparative examples, each of the following was prepared and analyzed in the same manner as above: an explant transplanted with an entire tooth germ tissue beneath a subrenal capsule (Comparative Example 1); an explant respectively transplanted with each of the epithelial tissue and mesenchymal tissue individually separated from a tooth germ (Comparative Example 2); an explant using a low-density aggregate containing an amount of a culture solution equal to the volume of the cells (Comparative Example 3); and an explant formed from a cell aggregate inside a support carrier by mixing epithelial cells and mesenchymal cells separated from a tooth germ without compartmentalization between the epithelial cells and the mesenchymal cells (Comparative Example 4). Further, in Comparative Example 4, after the epithelial cells and mesenchymal cells were gently mixed at the ratio of 1:1, one cell aggregate used for generation of a reconstituted tooth germ was prepared in the same way as in Examples 1 to 3.

(3) Histological Analysis

In the case of subrenal capsule transplantation, a reconstituted tooth germ along with surrounding kidney tissue was excised on the $7^{th}$ day or $14^{th}$ day after the transplantation, decalicified with 4.5% EDTA (pH 7.2) for 24 hours after being fixed with a 4% paraformaldehyde-phosphate buffer solution for 6 hours, and embedded in paraffin by a conventional method to produce a 10 μm section of a reconstituted tooth germ. For histological analysis, hematoxylin-eosin staining was performed according to a conventional method.

When a tooth germ derived from a GFP mouse was used for a reconstituted tooth germ, the tooth germ was deashed with 4.5% EDTA (pH 7.2) for 24 hours after being fixed in a 50% (w/v) sucrose-4% paraformaldehyde-phosphate buffer solution for 18 hours, embedded in an OCT compound (Miles Inc., Naperville, Ill.), and 10 μm sections were made with Cryostat (Leica, Wetzlar, Germany) to be observed under a fluorescence microscope (manufactured by Zeiss).

The results from the culture of the entire tooth germ tissue are shown in FIG. 3 and the results from the culture according to the generation method of the present invention are shown in FIGS. 4 to 7.

In Comparative Example 1, the entire excised tooth germ was transplanted beneath a subrenal capsule. As shown in FIG. 3, since the interaction between the mesenchymal cells and epithelial cells constituting the tooth germ is not impaired, enamel derived from the epithelial cells and dentin and dental pulp derived from the mesenchymal cells were formed, and a tooth was formed having a tip and root in addition to enamel and dentin arranged in given positions.

Figure 4:
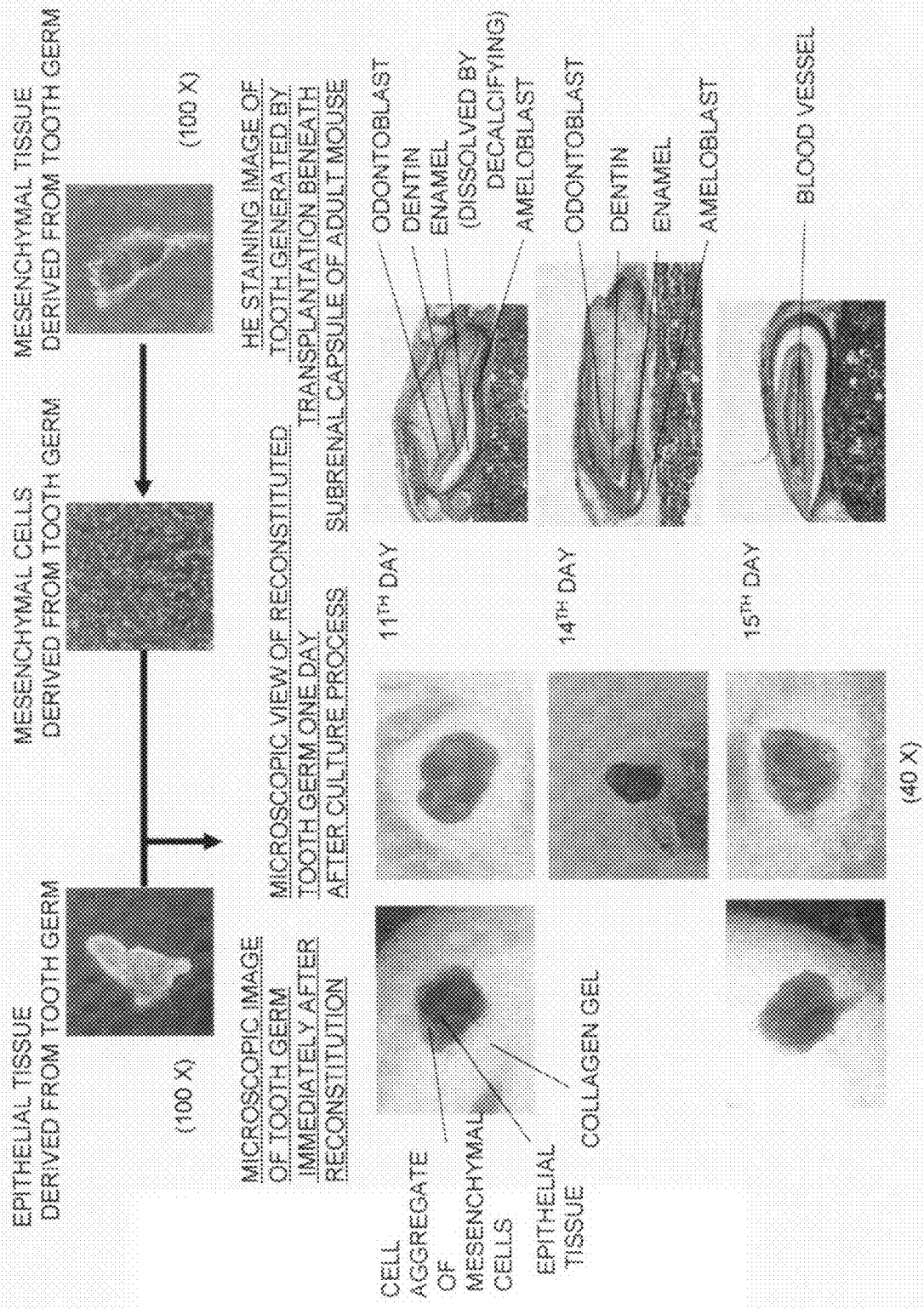
FIG. 4 shows phase contrast images of a tooth germ reconstituted by epithelial tissues derived from a tooth germ and mesenchymal cells derived from a tooth germ and time course staining images of a tooth produced by subrenal capsule transplantation of the reconstituted tooth germ, according to Example 1 of the present invention.
Figure 5:
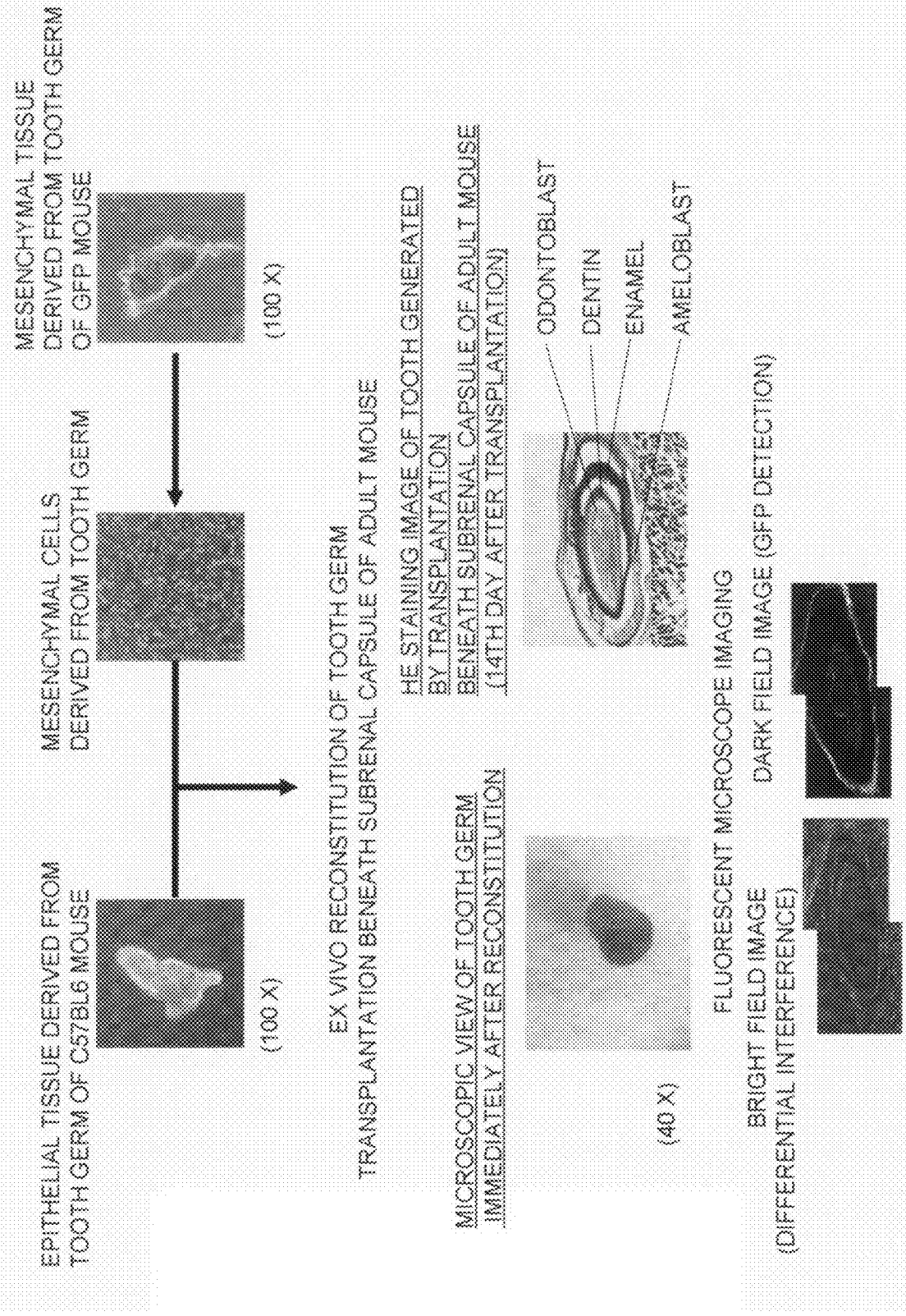
FIG. 5 shows phase contrast images of a tooth germ reconstituted by epithelial tissue derived from a tooth germ and mesenchymal cells derived from a tooth germ of a GFP mouse and a staining image of the $14^{th}$ day of the tooth produced by subrenal capsule transplantation of the reconstituted tooth germ, according to Example 1 of the present invention.
Figure 6:
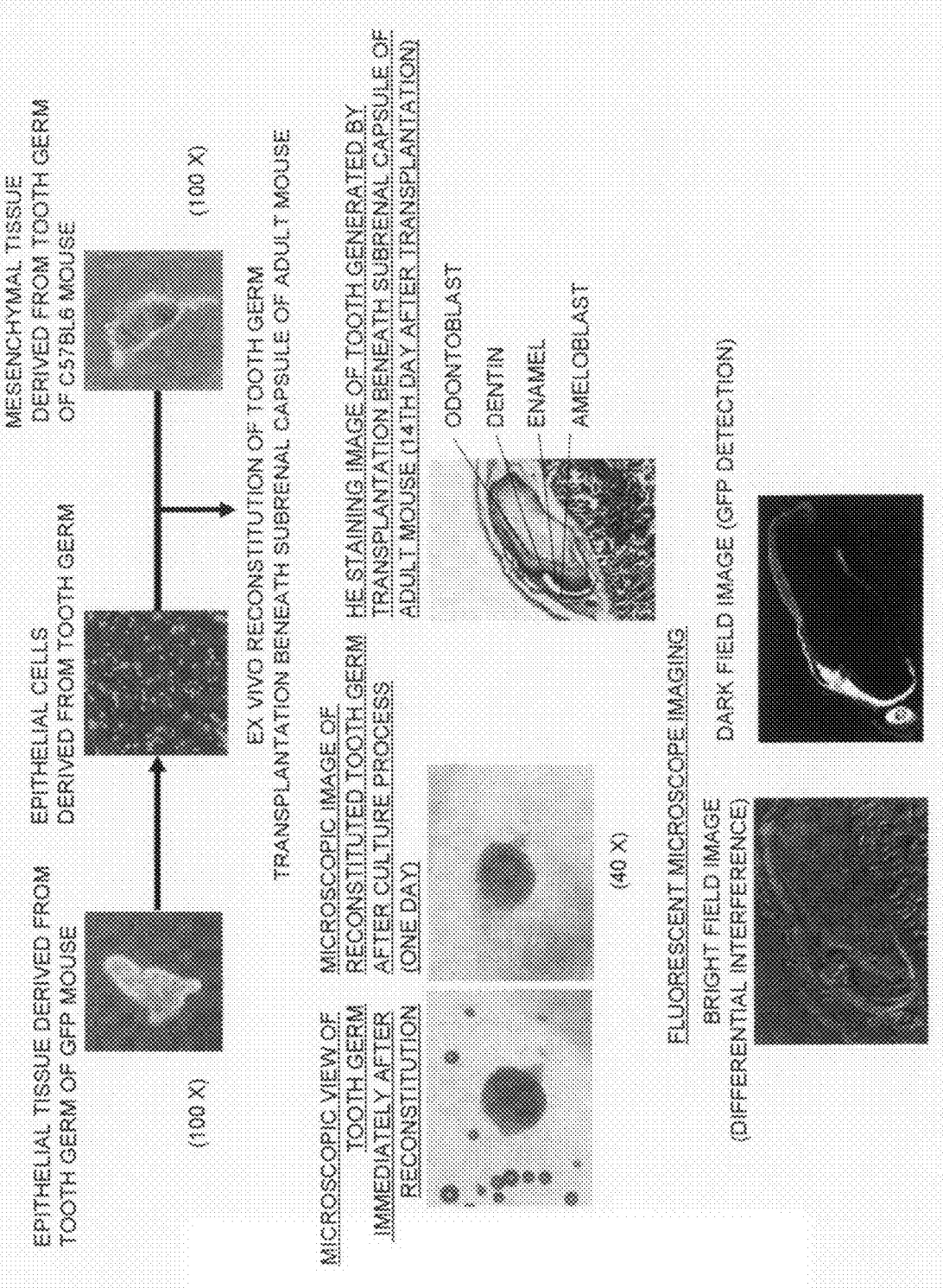
FIG. 6 shows phase contrast images of a tooth germ reconstituted by epithelial cells derived from a tooth germ of a GFP mouse and mesenchymal tissues derived from a tooth germ and a staining image of the $14^{th}$ day of the tooth produced by subrenal capsule transplantation of the reconstituted tooth germ, according to Example 2 of the present invention.

On the other hand, as shown in FIGS. 4 to 6, when a single cell form prepared from a tooth germ was used according to the present invention, in other words, when reconstitution was performed by combining tooth germ mesenchymal cells with tooth germ epithelial tissue (Example 1, see FIGS. 4 and 5) and by combining tooth germ mesenchymal tissue with tooth germ epithelial cells (Example 2, see FIG. 6), a tooth having a specific cell placement with dentin inside and enamel outside was generated by subrenal capsule transplantation in an 11- to 14-day period. The tooth obtained thereby demonstrated that it is possible to reconstitute the same kind of tooth as that generated normally by culturing an entire tooth germ (FIG. 3).

Furthermore, as shown in FIG. 4, with the present reconstitution and subrenal capsule transplantation, outer enamel, ameloblast, ameloblast, dentin, and odontoblast were easily identified on the $11^{th}$ day after the transplantation. The root portion was also the same as that from normal generation and alveolar bone was identified in the outer circumference of the root portion. Further, from the time course observation, dentin and odontoblast were easily identified on the $3^{rd}$ day after transplantation, and a tooth-specific structure had started to form in the tissue placement. In addition, on the $7^{th}$ day, accumulation of dentin, odontoblast, and ameloblast were in evidence, and the tooth generation progressed thereafter (data not shown).

Further, immediately after positioning inside a gel drop, it was observed under the microscope that cells constituting a cell aggregate were singly present, and after a single day of short culture, that the cells were strongly bonded and had changed into a single cohesive tissue as in the case of a normal excised tooth germ. This indicated that short culture prior to transplantation is effective in the formation of tooth.

Moreover, when mesenchymal cells derived from a GFP mouse were used, the cells were localized in dental pulp cells and odontoblasts derived from mesenchymal cells in the inner side (FIG. 5). On the other hand, when epithelial cells derived from a GFP mouse were used, the cells were localized in ameloblasts in the outer side, and the fluorescent images were congruous with those of the cell types used (FIG. 6). Therefore, it was obvious that the same cell interaction was performed as that in normal generation and that reconstitution of tissue was performed without sacrificing the directionality of the cells during the generation.

In addition, when organ culture was continued without applying subrenal capsule transplantation, a reconstituted tooth germ which was time course cultured from the beginning of the culture, gradually became larger, dentin and odontoblast were easily identified on the 16th day after the transplantation, and the formation of a tooth-specific structure was identified in the tissue placement (data not shown). This kind of construction by means of organ culture was identified not only when one or the other of epithelial cells and mesenchymal cells was used as tissue, but also when both were used.

Figure 7:
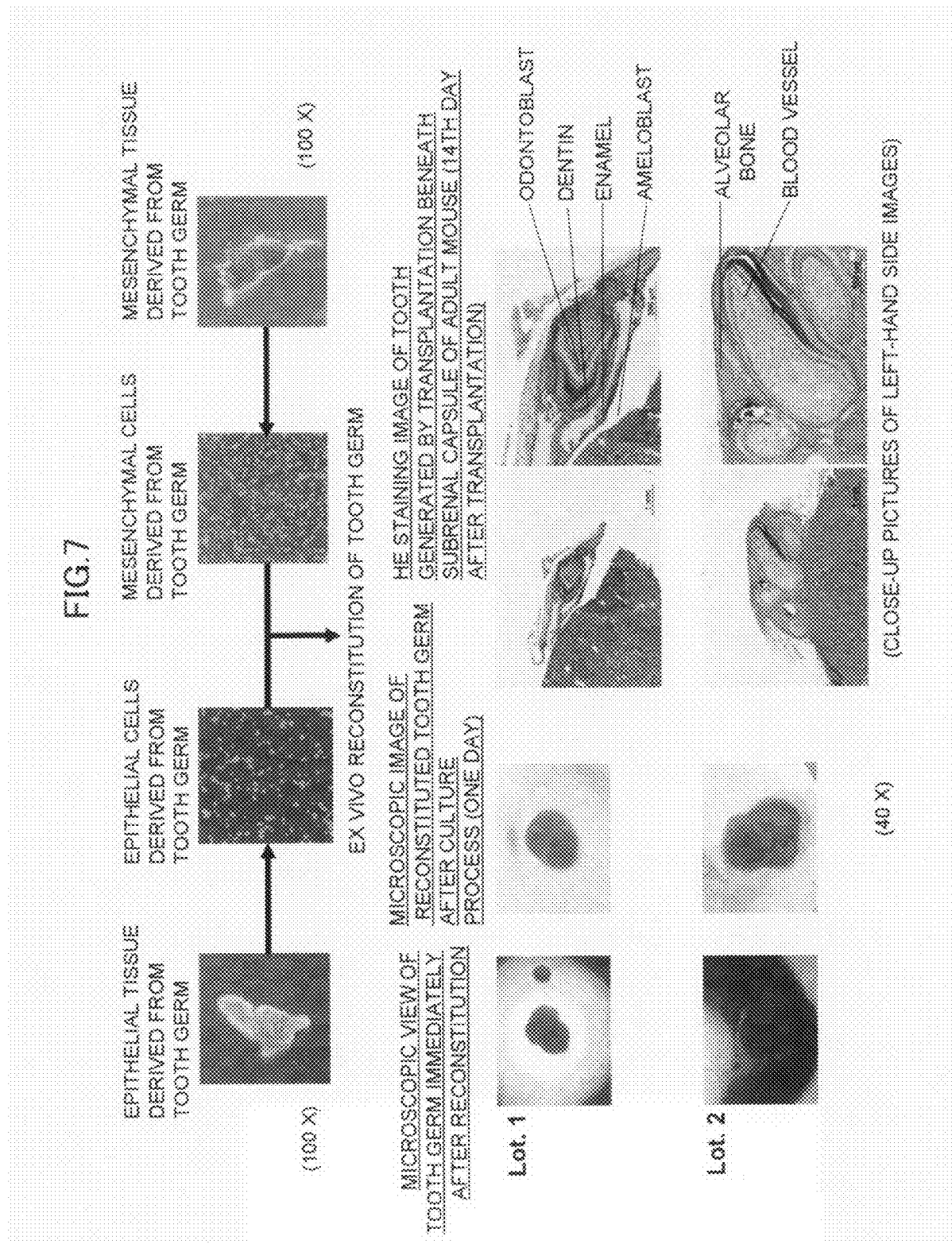
FIG. 7 shows phase contrast images of a tooth germ reconstituted by epithelial cells derived from a tooth germ and mesenchymal cells derived from a tooth germ and a staining image of the $14^{th}$ day of the tooth produced by subrenal capsule transplantation of the reconstituted tooth germ, according to Example 3 of the present invention.

Moreover, when tooth germ epithelial cells and tooth germ mesenchymal cells were used (Example 3), as shown in FIG. 7, the presence of dentin and enamel was confirmed, as when only one of tooth germ epithelial cells and tooth germ mesenchymal cells was used as tissue. When tooth germ epithelial cells and tooth germ mesenchymal cells were used, it was observed that plural teeth having directionality and structure were frequently generated from a single reconstituted tooth germ, suggesting the possibility of generating plural teeth by separating a tooth bud after generation. In particular, when tooth germ mesenchymal cells were first positioned inside a gel drop and then tooth germ epithelial cells were positioned so as to press against the tooth germ mesenchymal cells, the specific structure, where enamel and dentin are placed outside and inside, respectively, was more precisely constructed and the tooth shape formed more easily, and it was shown that this may be advantageous in tooth formation (data not shown).

Furthermore, when a tooth germ reconstituted by arranging epithelial cells and mesenchymal cells according to the present invention was organ cultured, the formation of plural tooth germs and/or tooth buds was frequently observed. This suggests the possibility of generating plural teeth from a single reconstituted tooth germ by surgically separating these plural tooth germs and/or tooth buds.

On the other hand, in the case of Comparative Example 2, when culture was performed with an epithelial tissue alone or an mesenchymal tissue alone, as shown in FIG. 8, a tooth with the specific structure mentioned above could not be constructed. Therefore, this suggests that tissue having the specific structure is reconstituted by performing cell interaction by the method of the present invention.

Figure 9:
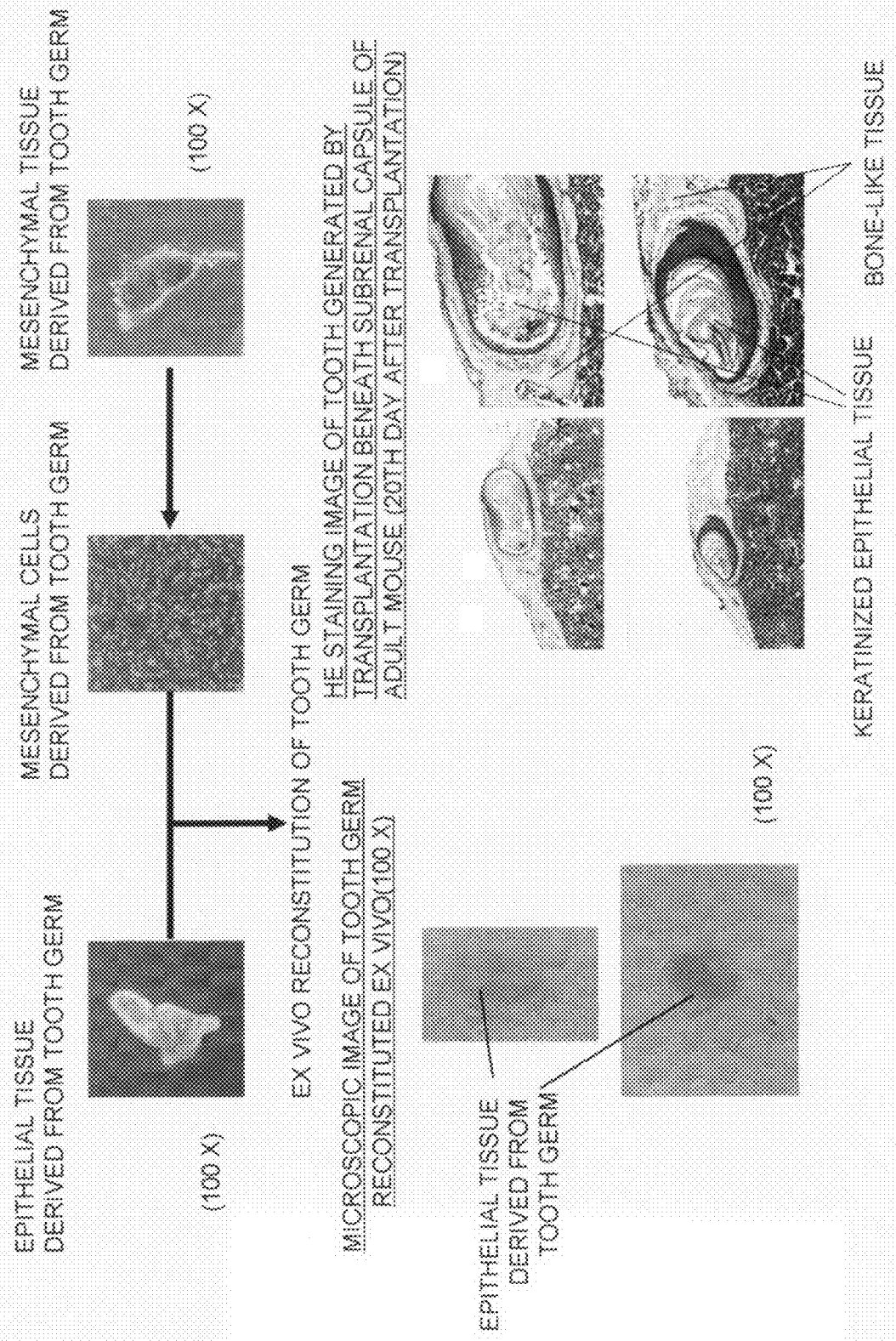
FIG. 9 shows phase contrast images of a low density tooth germ reconstituted by using epithelial tissues derived from a tooth germ and mesenchymal cells derived from a tooth germ and staining images of the $20^{th}$ day of subrenal capsule transplantation of the low density reconstituted tooth germ, according to Comparative Example 3 of the present invention.

Further, in the case of Comparative Example 3, where a low density cell aggregate was used, as shown in FIG. 9, single cells were already dispersed in a collagen gel drop during culture and the tooth specific structure was not reconstituted even by transplanting the cells beneath a subrenal capsule. This suggests that it is preferable to use cells at as high a density as possible in order to reconstitute a tooth by cell interaction.

Figure 10:
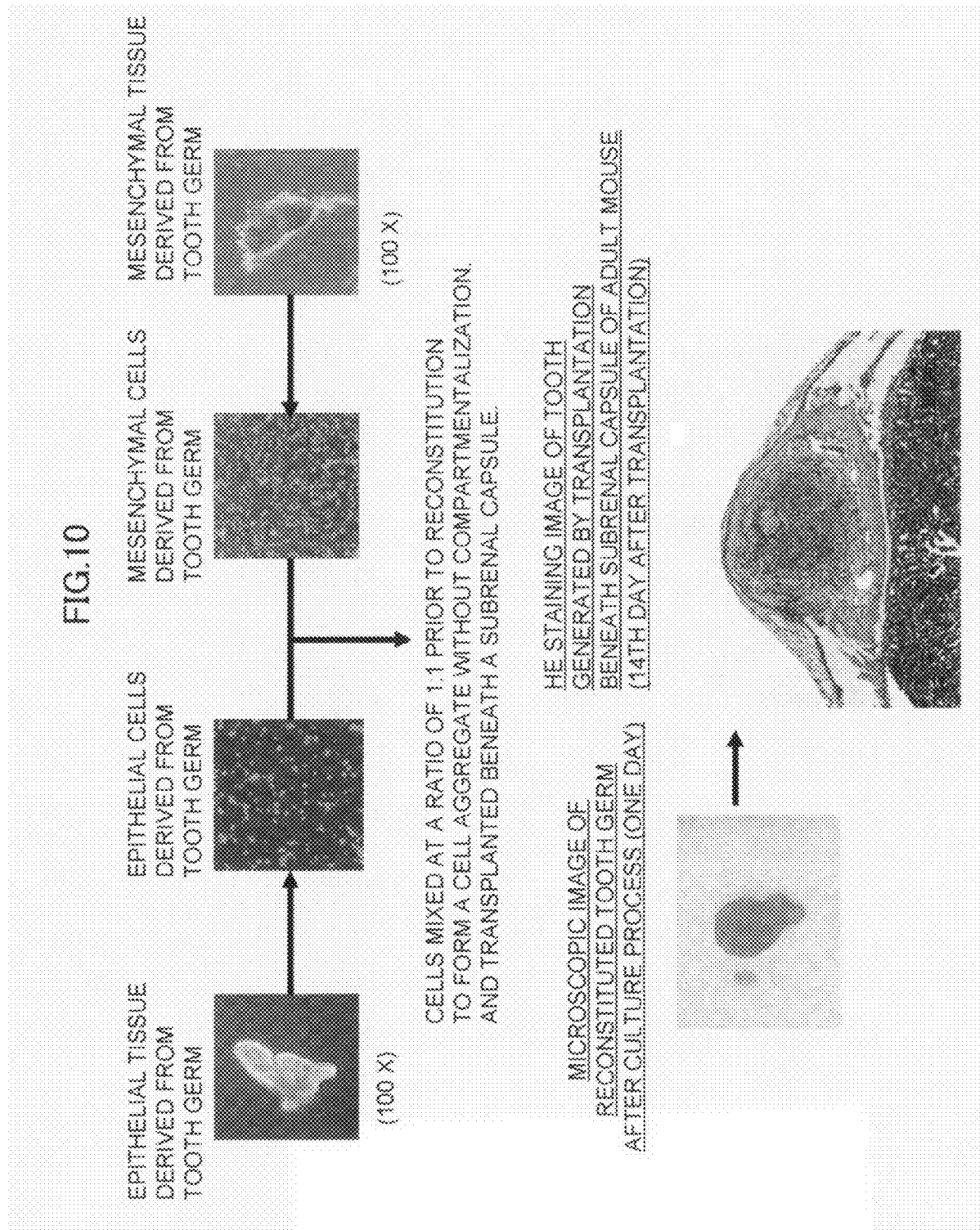
FIG. 10 shows phase contrast images of a tooth germ reconstituted by reconstituting epithelial tissues derived from a tooth germ and mesenchymal cells derived from a tooth germ in high density and without compartmentalization, and staining images of the $20^{th}$ day of subrenal capsule transplantation of the low density reconstituted tooth germ according to Comparative Example 4 of the present invention.

Further, in the case of Comparative Example 4, where a cell aggregate was formed at a high density by mixing tooth germ epithelial cells and tooth germ mesenchymal cells in advance in the ratio of 1:1 without compartmentalization, as shown in FIG. 10, hard tissue such as enamel and dentin were not identified. This suggests that it is important to form a cell aggregate compartmentalizing the mass of tooth germ epithelial cells and the mass of tooth germ mesenchymal cells, after the respective masses are prepared separately.

(4) Confirmation of Periodontal Tissue

Next, it was ascertained whether or not a tooth formed according to the present method had periodontal tissue. In situ hybridization as described below was used to confirm the presence of periodontal tissue in addition to the above-mentioned observation using HE staining images.

A reconstituted tooth germ transplanted beneath a subrenal capsule was excised on the $14^{th}$ day after transplantation, embedded in paraffin by a conventional method, and cut into 10 μm thickness sections. The paraffin was removed by soaking the sections in a xylene/ethanol dilution series. The sections were treated with 10 μg/ml of Protease K (Nacalai Tesque, Kyoto, Japan) in PBS (−) for 3 minutes and fixed with a 4% paraformaldehyde (Nacalai Tesque) phosphate buffer solution for 15 minutes. 0.1% (v/v) Triton X-100 (Sigma) was treated in PBS (−) for 3 minutes and washed with PBS (−) for 3 minutes. Then they were treated with 0.2N HCl (Wako) for 10 minutes and washed with PBS (−) and DEPC (diethyl pyrocarbonate) water respectively for 5 minutes each. After treatment with 1.5% (v/v) triethanol amine (Nacalai Tesque), 0.33N HCl (Wako), and 0.25% (v/v) acetic anhydride (Nacalai Tesque) in DEPC water for 10 minutes, the sections were washed twice with 2×SSC for 10 minutes. Periostin (Genbank accession No. NM#015784) probe was used by DIG-labeling cDNA section obtained with PCR using sense primer (−7; ggctgaagatggttcctctc, SEQ NO: 1) and antisense primer (573; gtacattgaaggaataacca, SEQ NO: 2). In situ hybridization was performed according to a conventional method, colorization was performed with an anti-DIG-Ap Fab fragment (Roche) and an NBT/BCIP Stock Sollution (Roche), and analysis was performed with an Axio Imager A. 1 (Zeiss) and AxioCam Mrc5 (Zeiss).

When the periodontal tissue in the above-mentioned Examples was examined in detail for the presence or absence of periodontal tissue, alveolar bone similar to that in the normal tooth germ transplantation of Comparative Example 1 (see FIG. 3) was formed around the tooth on the $14^{th}$ day after the transplantation in each of Examples 1 to 3, as shown in FIGS. 4 to 7.

Furthermore, as shown in FIG. 11, despite the combination of single cells and tissue, alveolar bone and periodontal membrane, which were similar to those in the normal tooth germ transplantation of Comparative Example 1, were formed around the obtained tooth in each of Examples 1 to 3. Further, when the tooth of Example 2 was observed, as shown in FIG. 12, expression of periostin mRNA, which is a periodontal membrane-specific gene, was identified in a region where the formation of periodontal membrane was identified by HE staining (the same was identified in Examples 1 and 3).

This indicates that a tooth germ prepared as in Examples 1 to 3 can form periodontal tissues such as alveolar bone and periodontal membrane.

Examples 4 and 5

Comparative Example 5

After completing the positioning process as described above, organ culture commonly used in culture processes was performed continuously for 14 days to analyze tooth generation. A combination of epithelial tissue and mesenchymal cells derived from a tooth germ was used in Example 4, and a combination of epithelial cells and mesenchymal cells derived from a tooth germ was used in Example 5. In addition, organ culture using a normal tooth germ was applied in Comparative Example 5. The results are shown in FIG. 13.

As shown in FIG. 13, in both of Examples 4 and 5, the size of the tooth germ increased as the culture period was lengthened and generation of a tooth having a specific structure approximately the same as that obtained by performing subrenal capsule transplantation was observed.

Moreover, in both of Examples 4 and 5, the teeth obtained from organ culture formed a set made up of plural teeth (for example, six teeth when mesenchymal cells and epithelial cells were used; FIG. 13, lowest row).

Examples 6 and 7

Comparative Example 6

As shown in Example 5, a tooth obtained from a reconstituted tooth germ was reinduced to form plural teeth despite the fact that the mesenchymal cells and the epithelial cells were prepared from a single reconstituted tooth germ. Analysis was performed to see whether each tooth reinduced simultaneously by the reconstituted tooth germ can grow into a single tooth.
(1) Analysis of Separation of Plural Tooth Germs Generated from Reconstituted Tooth Germs and Tooth Generation Potential
1) Individual Separation and Organ Culture of Tooth Germs Generated Plurally A reconstituted tooth germ obtained in a similar way to in Example 3 was organ cultured for 2 to 5 days, and plural tooth germs were generated from a single reconstituted tooth germ. Then, on the $2^{nd}$ day to $5^{th}$ day of the organ culture, single tooth germs were surgically separated from the reconstituted tooth germ that had generated plural tooth germs using an injection needle and tweezers under a stereomicroscope.

Gel drops were prepared by dropping 30 μL of Cellmatrix type I-A (Nitta gelatin, Osaka, Japan) onto a silicon grease coated Petri dish in the same way as in Example 1. Each of the above-mentioned individually separated tooth germs was placed inside a gel drop, and set still in a $CO_2$ incubator for 10 minutes to solidify the Cellmatrix type I-A (Nitta Gelatin). Each of the individually separated tooth germs, along with the surrounding gel, which was a support carrier, was transferred onto the membrane of a cell culture insert in a culture vessel, in which the cell culture insert (PET membrane of pore size of 0.4 micron; BD, Franklin Lakes, N.J.) was set so as to contact with DMEM (Sigma) supplemented by 10% FCS (JRH), and organ cultured for 18 to 24 hours.
2) Histological Analysis After culture, each of the individually separated tooth germs along with the surrounding gel was transplanted beneath a subrenal capsule of an 8 week-old C57BL/6 mouse and the individually separated tooth germs were excised on the $14^{th}$ day after the transplantation along with the surrounding kidney tissue. After the tissue was fixed with a 4% paraformaldehyde-phosphate buffer solution for 6 hours, the tissue was embedded in paraffin by a conventional method to make a 10 μm section. For histological analysis, hematoxylin-eosin staining was performed according to a conventional method.
3) Results The results of the histological analysis of the separated tooth germs, which were transplanted beneath a subrenal capsule to be generated for 14 days, are shown in FIG. 14. As shown in FIG. 14, each of the transplanted separated tooth germs was developed into a single tooth characterized by enamel, dentin, dental pulp, a crown and a root. Further, in the obtained teeth, the presence of enamel and dentin in the crown portion (see "a" on the middle and lower rows of FIG. 14) and an opening of the root in the root portion (see "b" on the mid row of FIG. 14) were observed.

These observations indicate that: ameloblast and odontoblast are present in the crown portion as in a normally generated tooth; the tooth has the same configuration as that of a normally generated tooth; and each tooth generated simultaneously as one of a set of teeth is the same as a normally generated tooth in terms of cell placement and directionality.
(2) Tooth Generation by Transplantation of a Reconstituted Tooth Germ into an Oral Cavity
1) Generation of Individually Separated Tooth Germs and Individually Separated Teeth Individually separated tooth germs were prepared from a reconstituted tooth germ, from which plural tooth germs were generated, on the $2^{nd}$ day to $5^{th}$ day of organ culture as described above. Further, plural teeth generated from the reconstituted tooth germ, which was transplanted beneath a subrenal capsule and excised after 14 days of transplantation, were surgically separated individually using an injection needle and tweezers under a stereomicroscope.

In the case of an individually separated tooth germ, a gel drop was prepared by dropping 30 μL of Cellmatrix type I-A (Nitta gelatin, Osaka, Japan), which was prepared at a concentration of 2.4 mg/ml in the above-mentioned culture solution, on to a silicon grease coated Petri dish as described above. The above-mentioned individually separated tooth germ was placed inside this gel drop, set still in a $CO_2$ incubator for 10 minutes to solidify the Cellmatrix type I-A (Nitta Gelatin). Next, the individually separated tooth germ along with the surrounding gel as a support carrier, was transferred onto the membrane of a cell culture insert in a culture vessel, in which the cell culture insert (PET membrane of pore size of 0.4 micron; BD, Franklin Lakes, N.J.) was set so as to be in contact with DMEM (Sigma) supplemented by 10% FCS (JRH), and organ cultured for 18 to 24 hours.

After the culture, the surrounding gel was surgically removed with an injection needle and tweezers, and the individually separated tooth germ was transplanted into a mandibular incisor extraction hole of an 8 week-old C57BL/6 mouse; and this was designated as Example 6. Further, a tooth individually separated from the reconstituted tooth germ which had been transplanted beneath a subrenal capsule was transplanted to a mandibular incisor extraction hole of an 8 week-old C57BL/6 mouse without being embedded in a gel after separation; and this was designated as Example 7.
2) Methods of Tooth Extraction of an Incisor and Transplantation into an Oral Cavity 3 days before transplantation into an oral cavity, an 8 week-old C57BL/6 mouse anesthetized with inhaled diethyl ether was injected intraperitoneally with a physiological salt solution containing 5 mg/ml pentobarbital sodium at a ratio of 200 μl to every 20 g of body weight. A mandible near the eruption site of a mandibular incisor of the mouse, whose sense of pain had been numbed, was exfoliated with a scalpel and a tip of the incisor embedded in the jaw bone was exposed. An incisor was extracted from the mandible using tweezers, blood was wiped off with absorbent cotton, and bleeding was arrested. For the sake of food ingestion, only the mandibular incisor on one side was extracted and comminuted feed for breeding was given every day.

An 8 week-old C57BL/6 mouse, whose tooth had been extracted by the above-mentioned method, was anesthetized with inhaled diethyl ether and a physiological salt solution containing 5 mg/ml pentobarbital sodium was injected intraperitoneally at a ratio of 200 µl to every 20 g of body weight. The mouse, whose sense of pain was numbed, was fixed on a dissecting table such that the side of the jaw, from which the tooth was extracted, would face up, and the mandible was exposed by cutting the skin and muscle layer from the side of the head in the area of the root portion of the hole left by the extracted tooth. A hole with a diameter of 1 mm in the case of an individually separated tooth germ and a hole with a diameter of 2 mm in the case of an individually separated tooth was made with a scalpel on the mandible covering the area of the root portion of the hole left by the extracted tooth, then the individually separated tooth germ or the individually separated tooth was transplanted into the area of the root portion of the hole left by the extracted tooth through the hole made with the scalpel. The orientation of the individually separated teeth germ or individually separated tooth to be transplanted was aligned with that of a normally generated tooth and also with the directionality of enamel and periodontal membrane seen in the mandibular incisors of adult mise. The cut muscle layer and skin were stitched up by a conventional method. The 8 week-old C57BL/6 mouse that had received the oral cavity transplantation was fed with comminuted feed for breeding every day.

In addition, Comparative Example 6 was designated as an example in which transplantation was not performed on a mouse was not transplanted.

3) Histological Analysis

The mandibles to which an individually separated tooth germ and individually separated tooth had been transplanted were excised on the 14$^{th}$ day after the oral cavity transplantation. The bone was deashed with 22.5% formic acid for 72 hours after being fixed with a 4% paraformaldehyde-phosphate buffer solution for 16 hours; then embedded in paraffin by a conventional method to make 10 µm sections. 50 ml of deashing solution was used for every two mandibles and the whole amount was replaced at the 48$^{th}$ hour of deashing. For the histological analysis, hematoxylin-eosin staining was performed according to a conventional method.

When a tooth germ derived from a C57BL/6 TgN (act-EGFP) OsbC14-Y01-FM131 mouse was used for an individually separated tooth germ and individually separated tooth, it was deashed with 22.5% formic acid for 72 hours after being fixed with a 4% paraformaldehyde-phosphate buffer solution for 16 hours, embedded in an OCT compound (Miles Inc., Naperville, Ill.) according to a conventional method, and 10 µm sections were made with Cryostat (Leica, Wetzlar, Germany) to be observed under a fluorescence microscope (Zeiss).

4) Results

Figure 15A:
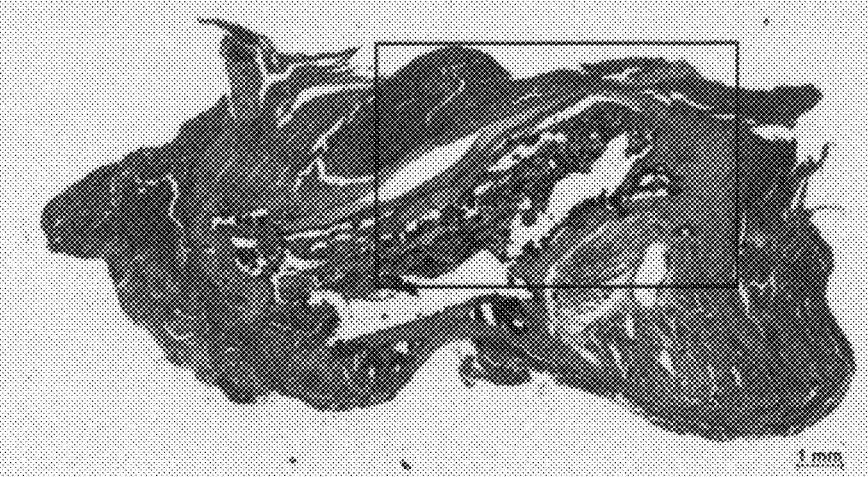
FIG. 15 (A) is a staining image of a non-transplant mouse on the 14th day after tooth extraction of the present invention and (B) is an enlarged view of the area enclosed by the frame of (A), according to Comparative Example 6.
Figure 15B:
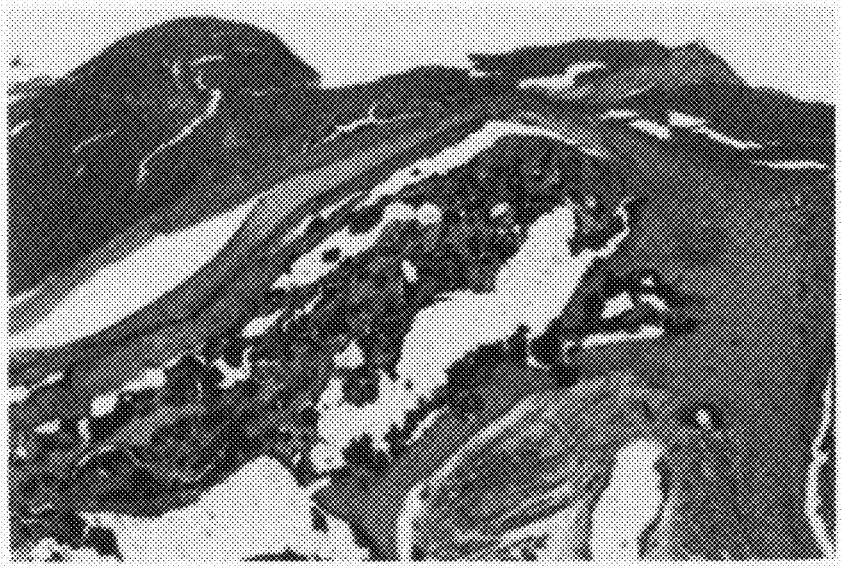

Histological pictures on the 14$^{th}$ day after the tooth extraction of a mouse in Comparative Example 6, in which transplantation was not performed on the mouse after the extraction of the incisor, are shown in FIG. 15, and histological pictures of an individually separated tooth germ (Example 6) and an individually separated tooth (Example 7) on the 14$^{th}$ day after transplantation into the hole left by an extracted incisor are shown in FIGS. 16 and 17, respectively.

As shown in FIG. 15, in the non-transplanted mouse of Comparative Example 6, only infiltrated cells and generated bone were identified and a tooth having hard tissue was not identified in a place corresponding to the transplantation site at the hole left by the extracted incisor.

On the other hand, as shown in FIG. 16, at the aforementioned site where an individually separated tooth germ was transplanted in Example 6, a tooth having enamel outside and dentin inside was generated. The generated tooth had a tooth tip and root, the directionality of a tooth, and the same structure as that of a normally generated tooth.

Moreover, in the mouse of Example 7, in which a tooth separated after generation due to subrenal capsule transplantation was transplanted into a hole left by an extracted tooth, as shown in FIG. 17, a tooth having enamel outside and dentin inside was generated at the aforementioned site. The generated tooth had a tooth tip and root, blood vessels inside dental pulp as well as periodontal membrane and alveolar bone around the tooth, and the same structure as that of a normally generated tooth.

Example 8 and Comparative Example 7

(1) Reconstitution of Hair Follicle

In order to demonstrate that the technology developed in the present invention is useful in formation of other organs as well as contributing to generation of a tooth germ, reconstitution of a hair follicle was performed. Mice were used as models for this experiment.

1) Method of Separating Cells

A hair follicle tissue of a maxillary whisker was excised from an embryo of fetal age of 14.5 days of a C57BL/6N mouse (purchased from CLEA Japan, Inc.) or a C57BL/6-TgN (act-EGFP) OsbC14-Y01-FM131 (RIKEN Bioresource Center) which is a Green Fluorescence Protein (EGFP) transgenic mouse, under a microscope by a conventional method. The hair follicle tissue of the maxillary whisker was washed with a phosphate buffer solution (PBS (−)) containing neither $Ca^{2+}$ nor $Mg^{2+}$, treated with an enzyme solution in which Dispase II (Roche, Mannheim, Germany) at a final concentration of 1.2 U/ml had been added to the PBS (−), at room temperature for 60 minutes, and then washed three times with DMEM (Sigma, St. Louis, Mo.) to which 10% of FCS (JRH Biosciences, Lenexa, Kans.) had been added. Furthermore, DNase I solution (Takara, Shiga, Japan) was added to make a final concentration of 70 U/ml to disperse the hair follicle tissue, and the hair follicle epithelial tissue and the hair follicle mesenchymal tissue were surgically separated, using a 25 G injection needle (Terumo, Tokyo, Japan).

For hair follicle epithelial cells, the hair follicle epithelial tissue obtained above was washed three times with PBS (−), and treated twice with an enzyme solution in which Collagenase I (Worthington, Lakewood, N.J.) at a final concentration of 100 U/ml was dissolved in the PBS (−), at 37° C. for 20 minutes. Cells precipitated and retrieved by centrifugation were further treated with 0.25% Trypsin (Sigma)-PBS (−) at 37° C. for 5 minutes. After washing the cells three times with DMEM supplemented by 10% FCS, DNase I solution at a final concentration of 70 U/ml was added to the cells, and single hair follicle epithelial cells were obtained by pipetting.

On the other hand, for hair follicle mesenchymal cells, the hair follicle mesenchymal tissue was washed three times with PBS (−) and treated with PBS (−) containing 0.25% Trypsin (Sigma) and 50 U/ml of Collagenase I (Worthington). 70 U/ml of DNase I (Takara) was added and single hair follicle mesenchymal cells were obtained by pipetting.

2) Method of Generating Reconstituted Hair Follicle

Next, cells used in generation of a reconstituted hair follicle were prepared in the same way as in Example 1, except that the hair follicle epithelial cells and hair follicle mesenchymal cells prepared above were used; 0.2 to 0.3 µL of each of the cells were applied to a collagen gel drop to prepare respective cell aggregates; and a reconstituted hair follicle was generated by positioning both cell aggregates in close contact with each other.

3) Subrenal Capsule Transplantation

For the reconstituted hair follicle generated in a gel, as in Example 1, the cell aggregates, together with the surrounding gel as a support carrier, were transferred onto a membrane of a cell culture insert in a culture vessel and organ cultured for 18 to 48 hours. After the organ culture, these were transplanted beneath a subrenal capsule of an 8 week-old C57BL/6 mouse to promote ectopic hair growth, and the hair growth was analyzed.

On the other hand, in Comparative Example 7, a single cell aggregate was prepared by mixing two types of cells ex vivo in the same way as in Comparative Example 4 except that hair follicle epithelial cells and hair follicle mesenchymal cells were used, and this was transplanted beneath a subrenal capsule as in Example 8.

4) Histological Analysis

In the case of subrenal capsule transplantation, a reconstituted hair follicle was excised along with the surrounding kidney tissue on the 14$^{th}$ day after the transplantation. In organ culture, the cell aggregate was retrieved on the 14$^{th}$ day of the culture. Then, the tissue or cell aggregate was fixed with a 4% paraformaldehyde phosphate buffer solution for 6 hours, and embedded in paraffin by a conventional method to make 10 μm sections. For histological analysis, hematoxylin-eosin staining was performed according to a conventional method.

5) Results

The results of the subrenal capsule transplantation of a hair follicle in the same type of mouse according to Example 8 are shown in FIG. 18. As shown in FIG. 18, a follicle, inner root sheath, and outer root sheath derived from epithelial cells and hair papilla cells derived from mesenchymal cells were identified on a longitudinal section of a hair follicle (section A) since the cell interaction between the epithelial cells and mesenchymal cells which constitute the initial hair follicle was not impaired when the reconstituted hair follicle was transplanted. Furthermore, in section A, although hair dissolved at the time of tissue staining, hair which was not completely dissolved was identified. On the cross section (section B), cell placement of an internal root sheath and external root sheath was identified such that epithelial cells might enclose pores. Since hair was dissolved at the time of tissue staining, the residue of hair dissolution was identified.

Figure 19:
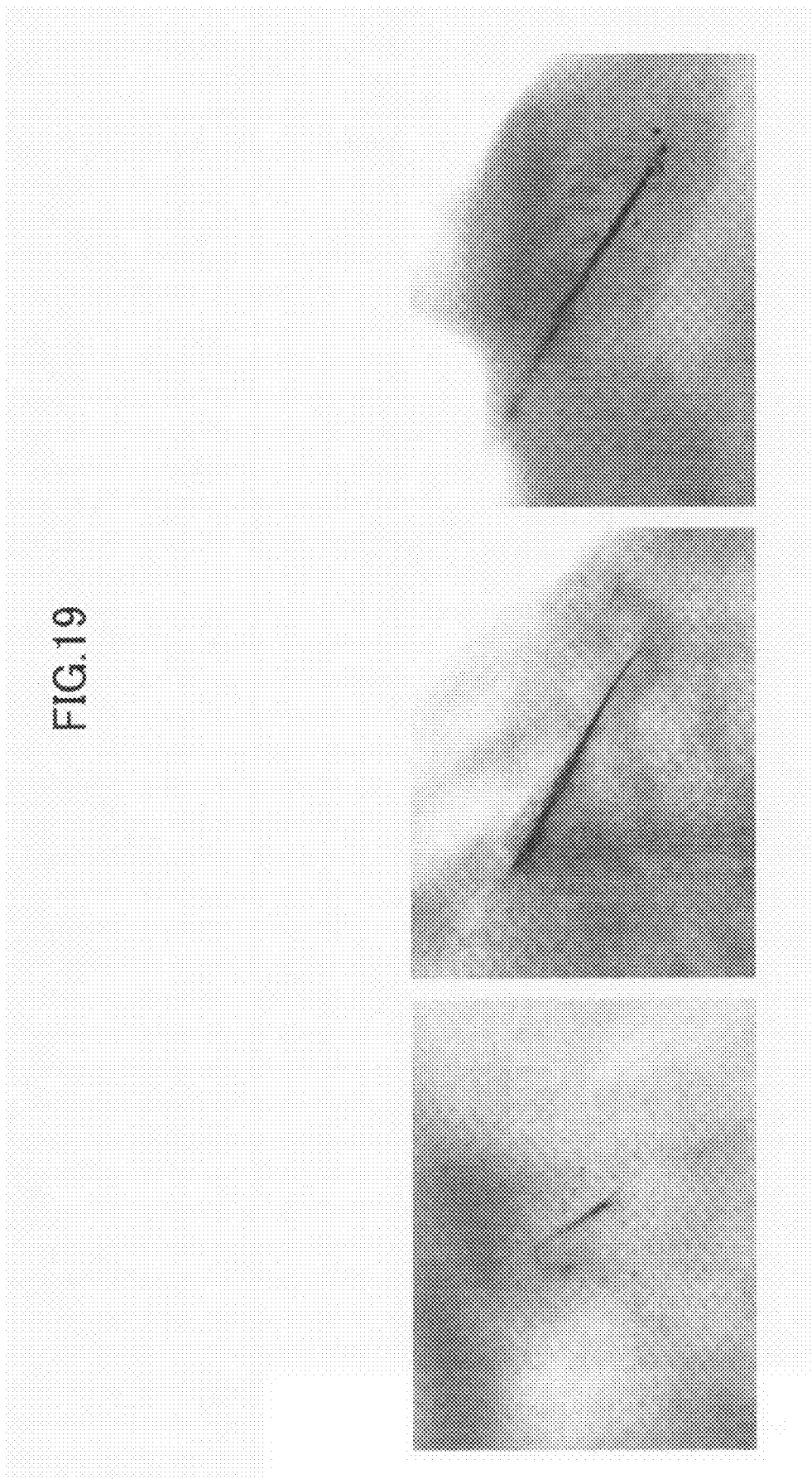
FIG. 19 shows stereoscopic microscope images of the 14th day of the hair follicle produced by subrenal capsule transplantation of the reconstituted hair follicle from epithelial cells derived from hair follicle tissue and mesenchymal cells derived from hair follicle tissue according to Example 8 of the present invention.

Moreover, as shown in FIG. 19, on an explant which was excised on the 14$^{th}$ day after the subrenal capsule transplantation of a reconstituted hair follicle, a hair grown from a hair follicle was identified.

On the other hand, in the case of Comparative Example 7, where epithelial cells and mesenchymal cells were mixed beforehand and reconstituted in a support carrier, a hair follicle tissue was not identified, as shown in FIG. 20.

Therefore, according to Example 8, hair could be generated from hair follicle tissue similarly to the cases in which a tooth was generated by using a tooth germ in Examples 1 to 7.

Thus, according to the present invention, it is shown that cell differentiation can be effectively induced and tissue having tissue-specific cell placement and directionality can be generated, by preparing epithelial tissue/cells and mesenchymal tissue/cells separately so that the interaction between the epithelial cells and the mesenchymal cells may effectively be performed and by compartmentalizing the tissue/cells and culturing them in contact with each other at high density, and not only for teeth and hair.

Therefore, according to the present invention, it is possible to artificially produce tissue constructed by cell interaction, because tissue can be reconstructed from various single cells without impairing cell interaction.

EXPLANATION OF LETTERS AND NUMERALS

10 gel pack (support carrier)
12 cell aggregate (a first cell mass)
14 cell aggregate (a second cell mass)
16 pipette tip

The invention claimed is:

1. A method of producing a tooth, comprising:

positioning a first cell mass substantially containing only either one of mesenchymal cells or epithelial cells, wherein at least one of the mesenchymal cells or the epithelial cells is derived from a tooth germ, and a second cell mass substantially containing only the other one of the mesenchymal cells or the epithelial cells, inside a support carrier, such that the first and second cell masses are in a state of close contact with each other inside the support carrier without mixing between the cell masses, wherein the mesenchymal cells or the epithelial cells are in close contact with each other in the corresponding cell mass;

positioning the first cell mass inside the support carrier such that the second cell mass makes a depression in the first cell mass such that the first cell mass substantially envelops the second cell mass when the second cell mass is inserted into the support carrier; and culturing the first and the second cell masses inside the support carrier until the tooth is formed, while maintaining the state of close contact between the cell masses.

2. The method of producing a tooth according to claim 1, wherein both the mesenchymal cells and the epithelial cells are derived from a tooth germ.

3. The method of producing a tooth according to claim 1, further comprising a first preparation process of preparing the first cell mass and a second preparation process of preparing the second cell mass prior to positioning the cell masses in contact with each other.

4. The method of producing a tooth according to claim 1, comprising conducting growth inside the support carrier in the presence of other cells of animals.

5. The method of producing a tooth according to claim 1, wherein each of the first cell mass and the second cell mass is a cell mass of single cells.

6. A method of producing a tooth with periodontal tissue comprising:

positioning a first cell mass substantially containing only either one of mesenchymal cells or epithelial cells, wherein at least one of the mesenchymal cells or the epithelial cells is derived from a tooth germ, and a second cell mass substantially containing only the other one of the mesenchymal cells or the epithelial cells, inside a support carrier, such that the first and the second cell masses are in a state of close contact with each other inside the support carrier without mixing between the cell masses, wherein the mesenchymal cells or the epithelial cells are in close contact with each other in the corresponding cell mass;

positioning the first cell mass inside the support carrier such that the second cell mass makes a depression in the first cell mass such that the first cell mass substantially envelops the second cell mass when the second cell mass is inserted into the support carrier;

culturing the first and the second cell masses inside the support carrier until the tooth is formed, while maintaining the state of close contact between the cell masses; and continuing the culturing until the periodontal tissue is formed.

7. A method of producing periodontal tissue, comprising:

positioning a first cell mass substantially containing only either one of mesenchymal cells or epithelial cells, wherein at least one of the mesenchymal cells or the epithelial cells is derived from a tooth germ, and a second cell mass substantially containing only the other one of the mesenchymal cells or the epithelial cells, inside a support carrier, such that the first and second cell masses are in a state of close contact with each other inside the support carrier without mixing between the cell masses, wherein the mesenchymal cells or the epithelial cells are in close contact with each other in the corresponding cell mass;

positioning the first cell mass inside the support carrier such that the second cell mass makes a depression in the first cell mass such that the first cell mass substantially envelops the second cell mass when the second cell mass is inserted into the support carrier;

culturing the first and the second cell masses inside the support carrier until a tooth and periodontal tissue contiguous to the tooth are obtained, while maintaining the state of close contact between the cell masses; and isolating the periodontal tissue obtained by the culturing.

8. A set of teeth, obtained by positioning a first cell mass substantially containing only either one of mesenchymal cells or epithelial cells, wherein at least one of the mesenchymal cells or the epithelial cells is derived from a tooth germ, and a second cell mass substantially containing only the other one of the mesenchymal cells or the epithelial cells, inside a support carrier, such that the first and the second cell masses are in a state of close contact with each other inside the support carrier without mixing between the cell masses, wherein the mesenchymal cells or the epithelial cells are in close contact with each other in the corresponding cell mass;

positioning the first cell mass inside the support carrier such that the second cell mass makes a depression in the first cell mass such that the first cell mass substantially envelops the second cell mass when the second cell mass is inserted into the support carrier; and culturing the first and the second cell masses inside the support carrier until the set of teeth is formed, while maintaining the state of close contact between the cell masses.

9. The set of teeth according to claim 8, wherein both the mesenchymal cells and the epithelial cells are derived from a tooth germ.

10. A method of producing a tissue that is constructed by an interaction between mesenchymal cells and epithelial cells, the method comprising:

positioning a first cell mass substantially containing only either one of mesenchymal cells or epithelial cells and a second cell mass substantially containing only the other one of the mesenchymal cells or the epithelial cells, inside a support carrier, such that the first and the second cell masses are in a state of close contact with each other inside the support carrier without mixing between the cell masses, wherein the mesenchymal cells or the epithelial cells are in close contact with each other in the corresponding cell mass;

positioning the first cell mass inside the support carrier such that the second cell mass makes a depression in the first cell mass such that the first cell mass substantially envelops the second cell mass when the second cell mass is inserted into the support carrier; and culturing the first and the second cell masses inside the support carrier until the tissue is formed, while maintaining the state of close contact between the cell masses.

11. The method of producing a tissue according to claim 10, further comprising a first preparation process of preparing the first cell mass and a second preparation process of preparing the second cell mass prior to positioning the cell masses in contact with each other.

12. The method of producing a tissue according to claim 10, wherein at least one of the mesenchymal cells and the epithelial cells is derived from a targeted tissue.

13. The method of producing a tissue according to claim 12, wherein the targeted tissue is selected from the group consisting of a tooth, a hair, a kidney, a lung and a liver.

14. A method of treatment for tooth loss or damage, comprising:
    transplanting at least one tooth selected from (i) a tooth obtained by the method of producing a tooth according to claim 1, and (ii) a tooth with periodontal tissue produced at the site of tooth loss or damage by the method of:
    (a) positioning a first cell mass substantially containing only either one of mesenchymal cells or epithelial cells, wherein at least one of the mesenchymal cells or the epithelial cells is derived from a tooth germ, and a second cell mass substantially containing only the other one of the mesenchymal cells or the epithelial cells, inside a support carrier and in contact with each other; and
    (b) culturing the first and the second cell masses inside the support carrier until a tooth and periodontal tissue contiguous to the tooth are obtained.

15. A method of treatment for tooth loss or damage, comprising:
    transplanting at least one tooth selected from (i) a tooth obtained by the method of producing a tooth according to claim 2, and (ii) a tooth with periodontal tissue produced at the site of tooth loss or damage by the method of:
    (a) positioning a first cell mass substantially containing only either one of mesenchymal cells or epithelial cells, wherein at least one of the mesenchymal cells or the epithelial cells is derived from a tooth germ, and a second cell mass substantially containing only the other one of the mesenchymal cells or the epithelial cells, inside a support carrier and in contact with each other; and
    (b) culturing the first and the second cell masses inside the support carrier until a tooth and periodontal tissue contiguous to the tooth are obtained.

16. A method of treatment for tooth loss or damage, comprising:
    transplanting at least one tooth selected from (i) a tooth obtained by the method of producing a tooth according to claim 3, and (ii) a tooth with periodontal tissue produced at the site of tooth loss or damage by the method of:
    (a) positioning a first cell mass substantially containing only either one of mesenchymal cells or epithelial cells, wherein at least one of the mesenchymal cells or the epithelial cells is derived from a tooth germ, and a second cell mass substantially containing only the other one of the mesenchymal cells or the epithelial cells, inside a support carrier and in contact with each other; and
    (b) culturing the first and the second cell masses inside the support carrier until a tooth and periodontal tissue contiguous to the tooth are obtained.

17. A method of treatment for tooth loss or damage, comprising:
    transplanting at least one tooth selected from (i) a tooth obtained by the method of producing a tooth according to claim 4, and (ii) a tooth with periodontal tissue produced at the site of tooth loss or damage by the method of:
    (a) positioning a first cell mass substantially containing only either one of mesenchymal cells or epithelial cells, wherein at least one of the mesenchymal cells or the epithelial cells is derived from a tooth germ, and a second cell mass substantially containing only the other one of the mesenchymal cells or the epithelial cells, inside a support carrier and in contact with each other; and
    (b) culturing the first and the second cell masses inside the support carrier until a tooth and periodontal tissue contiguous to the tooth are obtained.

18. A method of treatment for tooth loss or damage, comprising:
    transplanting at least one tooth selected from (i) a tooth obtained by the method of producing a tooth according to claim 5, and (ii) a tooth with periodontal tissue produced at the site of tooth loss or damage by the method of:
    (a) positioning a first cell mass substantially containing only either one of mesenchymal cells or epithelial cells, wherein at least one of the mesenchymal cells or the epithelial cells is derived from a tooth germ, and a second cell mass substantially containing only the other one of the mesenchymal cells or the epithelial cells, inside a support carrier and in contact with each other; and
    (b) culturing the first and the second cell masses inside the support carrier until a tooth and periodontal tissue contiguous to the tooth are obtained.

19. A method of treatment for tooth loss or damage, comprising:
    transplanting at least one tooth selected from (i) a tooth obtained by the method of producing a tooth according to claim 6, and (ii) a tooth with periodontal tissue produced at the site of tooth loss or damage by the method of:
    (a) positioning a first cell mass substantially containing only either one of mesenchymal cells or epithelial cells, wherein at least one of the mesenchymal cells or the epithelial cells is derived from a tooth germ, and a second cell mass substantially containing only the other one of the mesenchymal cells or the epithelial cells, inside a support carrier and in contact with each other; and
    (b) culturing the first and the second cell masses inside the support carrier until a tooth and periodontal tissue contiguous to the tooth are obtained.

20. The method of producing a tooth with periodontal tissue according to claim 6, wherein both the mesenchymal cells and the epithelial cells are derived from a tooth germ.

21. The method of producing a tooth with periodontal tissue according to claim 6, further comprising a first preparation process of preparing the first cell mass and a second preparation process of preparing the second cell mass prior to positioning the cell masses in contact with each other.

22. The method of producing a tooth with periodontal tissue according to claim 6, comprising conducting growth inside the support carrier in the presence of other cells of animals.

23. The method of producing a tooth with periodontal tissue according to claim 6, wherein each of the first cell mass and the second cell mass is a cell mass of single cells.

* * * * *

UNITED STATES PATENT AND TRADEMARK OFFICE
CERTIFICATE OF CORRECTION

| | | |
|---|---|---|
| PATENT NO. | : 8,361,709 B2 | Page 1 of 1 |
| APPLICATION NO. | : 11/921233 | |
| DATED | : January 29, 2013 | |
| INVENTOR(S) | : Tsuji et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1345 days.

Signed and Sealed this
Eighth Day of December, 2015

Michelle K. Lee
*Director of the United States Patent and Trademark Office*

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
ggctgaagat ggttcctctc                                               20

<210> SEQ ID NO 2
<211> LENGTH: 20
<212> TYPE: DNA
<213> ORGANISM: Artificial
<220> FEATURE:
<223> OTHER INFORMATION: antisense

<400> SEQUENCE: 2
gtacattgaa ggaataacca                                               20
```